United States Patent
Cushen et al.

(10) Patent No.: US 12,274,629 B2
(45) Date of Patent: Apr. 15, 2025

(54) BONE FRAGMENT COLLECTOR AND PROCESSOR

(71) Applicant: Stryker European Operations Limited, Carrigtwohill (IE)

(72) Inventors: Patrick Eoin Cushen, County Cork (IE); Johannes Jacobus Jacobs, Cork (IE); Garrett Daly, Cork (IE)

(73) Assignee: Stryker European Operations Limited, Carrigtwohill (IE)

( * ) Notice: Subject to any disclaimer, the term of this patent is extended or adjusted under 35 U.S.C. 154(b) by 369 days.

(21) Appl. No.: 17/757,512

(22) PCT Filed: Dec. 15, 2020

(86) PCT No.: PCT/IB2020/061983
§ 371 (c)(1),
(2) Date: Jun. 16, 2022

(87) PCT Pub. No.: WO2021/124117
PCT Pub. Date: Jun. 24, 2021

(65) Prior Publication Data
US 2023/0018045 A1    Jan. 19, 2023

Related U.S. Application Data

(60) Provisional application No. 62/949,863, filed on Dec. 18, 2019.

(51) Int. Cl.
*A61F 2/46* (2006.01)
*A61M 1/00* (2006.01)

(52) U.S. Cl.
CPC ............ *A61F 2/4644* (2013.01); *A61M 1/79* (2021.05); *A61F 2002/4649* (2013.01); *A61F 2002/4685* (2013.01); *A61M 2210/02* (2013.01)

(58) Field of Classification Search
CPC ............... A61B 17/1635; A61F 2/4644; A61F 2002/4645; A61F 2002/4649; A61M 1/79; A61M 2210/02
See application file for complete search history.

(56) References Cited

U.S. PATENT DOCUMENTS

| | | | |
|---|---|---|---|
| 1,199,350 | A | 9/1916 | Collin |
| 2,864,411 | A | 12/1958 | Stringfellow |

(Continued)

FOREIGN PATENT DOCUMENTS

| | | | |
|---|---|---|---|
| JP | 2005518923 A | 6/2005 | |
| JP | 2009508668 A | 3/2009 | |

(Continued)

OTHER PUBLICATIONS

English language abstract and machine-assisted English translation for WO 2015/158098 A1 extracted from espacenet.com database on Mar. 1, 2021, 12 pages.

(Continued)

*Primary Examiner* — Larry E Waggle, Jr.
(74) *Attorney, Agent, or Firm* — Howard & Howard Attorneys PLLC

(57) ABSTRACT

A device for collecting bone fragments includes a housing (512) and a filter element (522) disposed in the housing. The filter element has a first end (524), a second end (526), and a sidewall (528) that defines an inner peripheral (530) and outer peripheral (532) surface and includes a plurality of filter apertures (534). The inner peripheral surface at least partially defines a collection chamber (536) for collection of a composition comprising bone fragments. The outer peripheral surface of the sidewall and the housing are spaced apart from one another to define an exterior radial volume (540). The filter element also has a proximal portion (535) adjacent the second end (526) which defines at least one drain aperture (555). The composition is acquired and collected in (Continued)

the collection chamber with the exterior radial volume providing a primary fluid communication path with a vacuum source and the at least one drain aperture providing a supplementary fluid communication path with the vacuum source.

20 Claims, 28 Drawing Sheets

(56) References Cited

U.S. PATENT DOCUMENTS

| | | |
|---|---|---|
| 2,884,029 A | 4/1959 | Bruch |
| 2,959,797 A | 11/1960 | Harman |
| 2,978,001 A | 4/1961 | Whisler |
| 3,061,856 A | 11/1962 | Czapar |
| 3,081,770 A | 3/1963 | Hunter |
| 3,401,684 A | 9/1968 | Dremann |
| 3,561,429 A | 2/1971 | Jewett et al. |
| 3,581,336 A | 6/1971 | Herubel |
| 3,623,607 A | 11/1971 | Loos |
| 3,672,576 A | 6/1972 | Jefferson et al. |
| 3,699,604 A | 10/1972 | Hunt |
| 3,711,895 A | 1/1973 | Arendale |
| 3,785,380 A | 1/1974 | Brumfield |
| 3,813,775 A | 6/1974 | Fitzgerald |
| 3,815,604 A | 6/1974 | O'Malley et al. |
| 3,863,624 A | 2/1975 | Gram |
| 3,889,657 A | 6/1975 | Baumgarten |
| 3,890,712 A | 6/1975 | Lopez |
| 3,955,234 A | 5/1976 | Roefaro |
| 4,008,502 A | 2/1977 | Crane et al. |
| 4,018,686 A | 4/1977 | Shufflebarger et al. |
| 4,062,781 A | 12/1977 | Strauss et al. |
| 4,083,706 A | 4/1978 | Wiley |
| 4,141,142 A | 2/1979 | Karubian |
| 4,199,840 A | 4/1980 | Crane |
| 4,314,560 A | 2/1982 | Helfgott et al. |
| 4,393,086 A | 7/1983 | Masuyama |
| 4,428,748 A | 1/1984 | Peyman et al. |
| 4,449,271 A | 5/1984 | Karubian |
| 4,678,459 A | 7/1987 | Onik et al. |
| 4,685,472 A | 8/1987 | Muto |
| 4,701,259 A | 10/1987 | Rosaen |
| 4,753,634 A | 6/1988 | Johnson |
| 4,863,474 A | 9/1989 | Brown et al. |
| 4,886,492 A | 12/1989 | Brooke |
| 4,922,902 A | 5/1990 | Wuchinich et al. |
| 4,997,434 A | 3/1991 | Seedhom et al. |
| 5,040,542 A | 8/1991 | Gray |
| 5,085,659 A | 2/1992 | Rydell |
| 5,092,891 A | 3/1992 | Kummer et al. |
| 5,114,240 A | 5/1992 | Kindt-Larsen et al. |
| 5,152,744 A | 10/1992 | Krause et al. |
| 5,176,628 A | 1/1993 | Charles et al. |
| 5,192,439 A | 3/1993 | Roth et al. |
| 5,194,000 A | 3/1993 | Dury |
| 5,256,160 A | 10/1993 | Clement |
| 5,290,445 A | 3/1994 | Buttery |
| 5,335,671 A | 8/1994 | Clement |
| 5,392,790 A | 2/1995 | Kanner et al. |
| 5,429,596 A | 7/1995 | Arias et al. |
| 5,494,044 A | 2/1996 | Sundberg |
| 5,498,259 A | 3/1996 | Mourant et al. |
| 5,501,686 A | 3/1996 | Salyer |
| 5,512,045 A | 4/1996 | Gurchumelidze |
| 5,520,652 A | 5/1996 | Peterson |
| 5,542,918 A | 8/1996 | Atkinson |
| 5,554,111 A | 9/1996 | Morrey et al. |
| 5,569,178 A | 10/1996 | Henley |
| 5,630,939 A | 5/1997 | Bulard et al. |
| 5,669,394 A | 9/1997 | Bergey et al. |
| 5,704,909 A | 1/1998 | Morrey et al. |
| 5,766,134 A | 6/1998 | Lisak et al. |
| 5,830,359 A | 11/1998 | Knight et al. |
| 5,913,857 A | 6/1999 | Ritchart et al. |
| 5,954,961 A | 9/1999 | Carchidi |
| 5,957,881 A | 9/1999 | Peters et al. |
| 5,989,116 A | 11/1999 | Johnson et al. |
| 6,013,079 A | 1/2000 | Salam |
| 6,022,354 A | 2/2000 | Mercuri et al. |
| 6,039,748 A | 3/2000 | Savage et al. |
| 6,068,642 A | 5/2000 | Johnson et al. |
| 6,077,215 A | 6/2000 | Leysieffer |
| 6,083,175 A | 7/2000 | Lundgren |
| 6,113,569 A | 9/2000 | Becker |
| 6,183,254 B1 | 2/2001 | Cohen |
| 6,213,985 B1 | 4/2001 | Niedospial, Jr. |
| 6,270,703 B1 | 8/2001 | Wildman et al. |
| 6,276,115 B1 | 8/2001 | Kramer et al. |
| 6,276,936 B1 | 8/2001 | Forster et al. |
| 6,299,763 B1 | 10/2001 | Ashman |
| 6,382,976 B1 | 5/2002 | Wagner |
| 6,387,070 B1 | 5/2002 | Marino et al. |
| 6,406,454 B1 | 6/2002 | Hajianpour |
| 6,468,225 B1 | 10/2002 | Lundgren |
| 6,486,225 B1 | 11/2002 | Kamata et al. |
| 6,592,513 B1 | 7/2003 | Kroll et al. |
| 6,595,371 B1 | 7/2003 | Desmarais |
| 6,610,066 B2 | 8/2003 | Dinger et al. |
| 6,638,238 B1 | 10/2003 | Weber et al. |
| 6,641,582 B1 | 11/2003 | Hanson et al. |
| 6,712,773 B1 | 3/2004 | Viola |
| 6,723,102 B2 | 4/2004 | Johnson et al. |
| 6,749,636 B2 | 6/2004 | Michelson |
| 6,872,184 B2 | 3/2005 | Brannon |
| 6,875,166 B2 | 4/2005 | Kroll et al. |
| 6,908,455 B2 | 6/2005 | Hajianpour |
| 6,989,031 B2 | 1/2006 | Michelson |
| 7,033,359 B2 | 4/2006 | Meller |
| 7,175,336 B2 * | 2/2007 | Voellmicke ............ A61F 2/4601 366/189 |
| 7,195,617 B2 | 3/2007 | Papendick et al. |
| 7,204,810 B2 | 4/2007 | Hynes et al. |
| 7,214,059 B2 | 5/2007 | Takahashi |
| 7,244,263 B2 | 7/2007 | Robison et al. |
| 7,465,278 B2 | 12/2008 | Cicenas et al. |
| 7,497,340 B2 | 3/2009 | Hershberger et al. |
| 7,611,536 B2 | 11/2009 | Michelson |
| 7,615,037 B2 | 11/2009 | Murray et al. |
| 7,621,898 B2 * | 11/2009 | Lalomia ................ A61M 1/742 604/326 |
| 7,621,917 B2 | 11/2009 | Geneve et al. |
| 7,682,378 B2 | 3/2010 | Truckai et al. |
| 7,758,556 B2 | 7/2010 | Perez-Cruet et al. |
| 7,806,834 B2 | 10/2010 | Beckman et al. |
| 7,819,819 B2 | 10/2010 | Quick et al. |
| 7,828,748 B2 | 11/2010 | Hibner |
| 7,854,706 B2 | 12/2010 | Hibner |
| 7,909,822 B2 | 3/2011 | Guerra |
| 7,918,804 B2 | 4/2011 | Monson et al. |
| 7,955,057 B2 | 6/2011 | Kuehner et al. |
| 7,971,728 B2 | 7/2011 | Anspach et al. |
| 8,016,846 B2 | 9/2011 | McFarlin et al. |
| 8,043,291 B2 | 10/2011 | Accordino |
| 8,070,689 B2 | 12/2011 | Masseglia et al. |
| 8,088,291 B2 | 1/2012 | Hershberger et al. |
| 8,100,874 B1 | 1/2012 | Jordan et al. |
| 8,137,403 B2 | 3/2012 | Michelson |
| 8,192,488 B2 | 6/2012 | Lesinski et al. |
| 8,221,316 B2 | 7/2012 | DeGould |
| 8,241,335 B2 | 8/2012 | Truckai et al. |
| 8,277,393 B2 | 10/2012 | Miller et al. |
| 8,292,909 B1 | 10/2012 | DuBois et al. |
| 8,298,254 B2 | 10/2012 | Dubois et al. |
| 8,308,746 B2 | 11/2012 | Pravong et al. |
| 8,357,163 B2 | 1/2013 | Sidebotham et al. |
| 8,366,694 B1 | 2/2013 | Jordan |
| 8,403,931 B2 | 3/2013 | Sidebotham et al. |
| 8,414,586 B2 | 4/2013 | Cawthan et al. |
| 8,449,545 B2 | 5/2013 | Sidebotham et al. |
| 8,485,986 B2 | 7/2013 | Lampropoulos et al. |
| 8,518,002 B2 | 8/2013 | Murray et al. |
| 8,518,043 B2 | 8/2013 | Sidebotham et al. |

(56) References Cited

U.S. PATENT DOCUMENTS

| | | |
|---|---|---|
| 8,523,866 B2 | 9/2013 | Sidebotham et al. |
| 8,529,570 B2 | 9/2013 | Mehdizade |
| 8,535,316 B2 | 9/2013 | Lewis et al. |
| D690,813 S | 10/2013 | Bizzell et al. |
| D690,814 S | 10/2013 | Bizzell et al. |
| 8,556,897 B2 | 10/2013 | Sidebotham et al. |
| 8,562,607 B2 | 10/2013 | Truckai et al. |
| 8,622,953 B2 | 1/2014 | Hynes et al. |
| 8,636,837 B2 | 1/2014 | Nonnenmacher |
| 8,647,574 B2 | 2/2014 | Halverson et al. |
| 8,657,842 B2 | 2/2014 | Dubois et al. |
| 8,721,595 B2 | 5/2014 | Stiehl et al. |
| 8,740,908 B2 | 6/2014 | Farley et al. |
| 8,790,321 B2 | 7/2014 | Segina et al. |
| 8,815,099 B1 | 8/2014 | Dubois et al. |
| 8,840,614 B2 | 9/2014 | Mikhail et al. |
| 8,845,604 B2 | 9/2014 | Croizat et al. |
| 8,845,605 B2 | 9/2014 | Hensler et al. |
| 8,887,770 B1 | 11/2014 | Shippert |
| 8,915,921 B2 | 12/2014 | Ralph et al. |
| 8,920,393 B2 | 12/2014 | Hensler et al. |
| 8,932,358 B1 | 1/2015 | Nehls |
| 8,956,358 B2 | 2/2015 | Cannell et al. |
| 9,034,044 B2 | 5/2015 | Hensler |
| 9,089,801 B1 | 7/2015 | Gavlak et al. |
| 9,248,025 B2 | 2/2016 | Dinville |
| 9,326,778 B2 | 5/2016 | Huwais |
| 9,358,327 B1 | 6/2016 | Venturi |
| 9,504,454 B2 | 11/2016 | Al-Khatib |
| 9,532,796 B2 | 1/2017 | Dubois et al. |
| 9,555,169 B2 | 1/2017 | Segina et al. |
| 9,636,235 B2 | 5/2017 | Hensler |
| 9,693,843 B2 | 7/2017 | Cohen |
| 9,750,265 B1 | 9/2017 | Bullard et al. |
| 9,763,731 B2 | 9/2017 | Dubois et al. |
| 9,770,289 B2 | 9/2017 | Dubois et al. |
| 9,777,257 B2 | 10/2017 | Howard et al. |
| 9,782,259 B2 | 10/2017 | Mikhail et al. |
| 9,795,723 B2 | 10/2017 | Gavlak et al. |
| 9,833,246 B2 | 12/2017 | Hensler et al. |
| 9,833,297 B2 | 12/2017 | Hensler et al. |
| 9,867,914 B2 | 1/2018 | Bonano et al. |
| 9,872,944 B1 | 1/2018 | Willard et al. |
| 9,907,568 B2 | 3/2018 | Tramboo et al. |
| 9,925,068 B2 | 3/2018 | Bays et al. |
| 10,039,621 B2 | 8/2018 | Huwais |
| 10,058,393 B2 | 8/2018 | Bonutti et al. |
| 10,166,107 B2 | 1/2019 | Wendelburg |
| 10,369,258 B2 | 8/2019 | Hensler et al. |
| 10,493,183 B2 | 12/2019 | Hensler et al. |
| 10,953,360 B2 | 3/2021 | Ouyang et al. |
| 2002/0177785 A1 | 11/2002 | Brannon |
| 2002/0183758 A1 | 12/2002 | Middleton et al. |
| 2003/0130594 A1 | 7/2003 | Hynes et al. |
| 2003/0176778 A1 | 9/2003 | Messing et al. |
| 2004/0034339 A1 | 2/2004 | Stoller et al. |
| 2004/0049217 A1 | 3/2004 | Ross et al. |
| 2004/0092992 A1 | 5/2004 | Adams et al. |
| 2004/0167529 A1 | 8/2004 | Papendick et al. |
| 2004/0178129 A1 | 9/2004 | Rizzo |
| 2004/0225266 A1 | 11/2004 | Tapadiya |
| 2004/0243145 A1 | 12/2004 | Bobo, Sr. |
| 2005/0203527 A1 | 9/2005 | Carrison et al. |
| 2005/0261692 A1 | 11/2005 | Carrison et al. |
| 2006/0004369 A1 | 1/2006 | Patel et al. |
| 2006/0052760 A1 | 3/2006 | Batzdorf |
| 2006/0056270 A1 | 3/2006 | Lee |
| 2006/0100706 A1 | 5/2006 | Shadduck et al. |
| 2006/0106353 A1 | 5/2006 | Geneve et al. |
| 2006/0122615 A1 | 6/2006 | McKinley |
| 2006/0129062 A1 | 6/2006 | Nicoson et al. |
| 2006/0229550 A1 | 10/2006 | Staid et al. |
| 2007/0010892 A1 | 1/2007 | Ogiso |
| 2007/0016217 A1 | 1/2007 | Dinville |
| 2007/0055259 A1 | 3/2007 | Norton et al. |
| 2007/0100277 A1 | 5/2007 | Shippert |
| 2007/0149895 A1 | 6/2007 | McCullough et al. |
| 2007/0162062 A1 | 7/2007 | Norton et al. |
| 2007/0203471 A1 | 8/2007 | Anspach et al. |
| 2007/0208348 A1 | 9/2007 | Parmigiani |
| 2007/0225665 A1 | 9/2007 | Perez-Cruet et al. |
| 2007/0233131 A1 | 10/2007 | Song et al. |
| 2008/0214955 A1 | 9/2008 | Speeg et al. |
| 2008/0294166 A1 | 11/2008 | Goldin et al. |
| 2008/0294167 A1 | 11/2008 | Schumacher et al. |
| 2009/0127183 A1 | 5/2009 | Lauer |
| 2009/0220914 A1 | 9/2009 | Gershenzon |
| 2009/0280452 A1 | 11/2009 | Garfinkel |
| 2009/0304764 A1 | 12/2009 | Breckwoldt |
| 2010/0057217 A1 | 3/2010 | Breimesser et al. |
| 2010/0063416 A1 | 3/2010 | Cicenas et al. |
| 2010/0076439 A1 | 3/2010 | Hatch |
| 2010/0094360 A1 | 4/2010 | Elwatidy |
| 2010/0152611 A1 | 6/2010 | Parihar et al. |
| 2010/0190138 A1 | 7/2010 | Giorno |
| 2010/0241125 A1 | 9/2010 | Termanini |
| 2010/0297577 A1 | 11/2010 | Cohen |
| 2010/0298835 A1 | 11/2010 | Ralph et al. |
| 2011/0054349 A1 | 3/2011 | Hibner |
| 2011/0098596 A1 | 4/2011 | Ozturk et al. |
| 2011/0112515 A1 | 5/2011 | Stiehl et al. |
| 2011/0160731 A1 | 6/2011 | Bleich et al. |
| 2011/0195380 A1 | 8/2011 | Giorno |
| 2012/0109227 A1 | 5/2012 | Farley et al. |
| 2012/0279933 A1 | 11/2012 | Hensler et al. |
| 2012/0330220 A1 | 12/2012 | Hensler et al. |
| 2013/0023880 A1 | 1/2013 | Tramboo et al. |
| 2013/0046199 A1 | 2/2013 | Dubois et al. |
| 2013/0123721 A1 | 5/2013 | Stiehl et al. |
| 2013/0172919 A1 | 7/2013 | Carrison |
| 2013/0211321 A1 | 8/2013 | Dubois et al. |
| 2013/0211438 A1 | 8/2013 | Dubois et al. |
| 2013/0273500 A1 | 10/2013 | Giorno |
| 2013/0304003 A1 | 11/2013 | Stiehl et al. |
| 2014/0271654 A1 | 9/2014 | Li et al. |
| 2014/0277188 A1 | 9/2014 | Poulos |
| 2014/0363403 A1 | 12/2014 | Segina et al. |
| 2015/0038973 A1 | 2/2015 | Grim |
| 2015/0045799 A1 | 2/2015 | Budyansky et al. |
| 2015/0090652 A1 | 4/2015 | Hensler et al. |
| 2015/0164518 A1 | 6/2015 | Jinton et al. |
| 2015/0335785 A1 | 11/2015 | Ayers |
| 2016/0008007 A1 | 1/2016 | Taha |
| 2016/0067047 A1 | 3/2016 | Wendelburg |
| 2016/0220389 A1 | 8/2016 | Dinville |
| 2016/0324530 A1 | 11/2016 | Assell et al. |
| 2016/0325018 A1 | 11/2016 | Assell et al. |
| 2016/0367734 A1 | 12/2016 | Gavlak et al. |
| 2017/0065377 A1 | 3/2017 | Hall et al. |
| 2017/0071703 A1 | 3/2017 | Hall et al. |
| 2017/0112978 A1 | 4/2017 | Segina et al. |
| 2017/0202559 A1 | 7/2017 | Taha |
| 2017/0202579 A1 | 7/2017 | Abrahams et al. |
| 2017/0231785 A1 | 8/2017 | Hensler |
| 2017/0325908 A1 | 11/2017 | Starkey |
| 2018/0000593 A1 | 1/2018 | Arbuck |
| 2018/0043068 A1 | 2/2018 | Willard et al. |
| 2018/0064857 A1 | 3/2018 | Gavlak et al. |
| 2018/0078297 A1 | 3/2018 | Giorno |
| 2018/0098776 A1 | 4/2018 | Sidebotham et al. |
| 2018/0110404 A1 | 4/2018 | Devaiah et al. |
| 2018/0125548 A1 | 5/2018 | Taylor et al. |
| 2018/0206857 A1 | 7/2018 | Chenaux et al. |
| 2018/0325527 A1 | 11/2018 | Wozencroft |
| 2019/0167869 A1 | 6/2019 | Willard et al. |
| 2021/0113351 A1 | 4/2021 | Lambarth et al. |
| 2021/0196865 A1* | 7/2021 | Cushen ............ A61M 1/63 |

FOREIGN PATENT DOCUMENTS

| | | |
|---|---|---|
| JP | 2017526522 A | 9/2017 |
| WO | 9001303 A2 | 2/1990 |
| WO | 9309731 A1 | 5/1993 |
| WO | 9314700 A1 | 8/1993 |

(56) References Cited

FOREIGN PATENT DOCUMENTS

| | | | |
|---|---|---|---|
| WO | 9628109 A1 | 9/1996 | |
| WO | 9726835 A1 | 7/1997 | |
| WO | 0197949 A1 | 12/2001 | |
| WO | 02069838 A1 | 9/2002 | |
| WO | 02078514 A2 | 10/2002 | |
| WO | 02102254 A2 | 12/2002 | |
| WO | 03068078 A1 | 8/2003 | |
| WO | 03073945 A1 | 9/2003 | |
| WO | 2005092252 A1 | 10/2005 | |
| WO | 2006102555 A2 | 9/2006 | |
| WO | 2007083850 A1 | 7/2007 | |
| WO | 2008094439 A2 | 8/2008 | |
| WO | 2008094444 A2 | 8/2008 | |
| WO | 2009024798 A1 | 2/2009 | |
| WO | 2012003383 A1 | 1/2012 | |
| WO | 2012093810 A2 | 7/2012 | |
| WO | 2013002530 A2 | 1/2013 | |
| WO | 2013019954 A1 | 2/2013 | |
| WO | 2013035915 A1 | 3/2013 | |
| WO | 2013104682 A1 | 7/2013 | |
| WO | 2014210350 A1 | 12/2014 | |
| WO | 2015154060 A2 | 10/2015 | |
| WO | 2015158098 A1 | 10/2015 | |
| WO | 2016014955 A1 | 1/2016 | |
| WO | 2016183017 A1 | 11/2016 | |
| WO | 2016183019 A1 | 11/2016 | |
| WO | 2017066720 A1 | 4/2017 | |
| WO | 2017197057 A1 | 11/2017 | |
| WO | 2018227311 A2 | 12/2018 | |
| WO | 2019033259 A1 | 2/2019 | |
| WO | WO-2019239375 A2 * | 12/2019 | ......... A61B 17/1635 |

OTHER PUBLICATIONS

English language abstract and machine-assisted English translation for WO 2019/033259 A1 extracted from espacenet.com database on Mar. 1, 2021, 8 pages.
English language abstract for WO 02/069838 A1 extracted from espacenet.com database on Mar. 1, 2021, 2 pages.
English language abstract for WO 2012/093810 A2 and machine-assisted English translation for equivalent KR 101183829 B1 extracted from espacenet.com database on Mar. 1, 2021, 10 pages.
English language abstract for WO 2013/002530 A2 and machine-assisted English translation for equivalent KR 1011338388 B2 extracted from espacenet.com database on Mar. 1, 2021, 11 pages.
English language abstract for WO 2013/035915 A1 and machine-assisted English translation for equivalent KR 101266187 B1 extracted from espacenet.com database on Mar. 1, 2021, 16 pages.
English language abstract for WO 90/01303 A2 extracted from espacenet.com database on Mar. 1, 2021, 1 page.
International Search Report for Application No. PCT/IB2019/054972 dated Dec. 13, 2019, 3 pages.
International Search Report for Application No. PCT/IB2020/061983 dated Apr. 22, 2021, 3 pages.
International Search Report for Application No. PCT/US2019/027621 dated Aug. 2, 2019, 5 pages.
Partial International Search Report for Application No. PCT/IB2020/061983 dated Mar. 1, 2021, 2 pages.
English language abstract for JP 2005-518923 A extracted from espacenet.com database on Feb. 27, 2023, 1 bage.
English language abstract for JP 2009-0127183 A extracted from espacenet.com database on Feb. 27, 2023, 1 page.
English language abstract for JP 2017-526522 A extracted from espacenet.com database on Feb. 27, 2023, 2 pages.

* cited by examiner

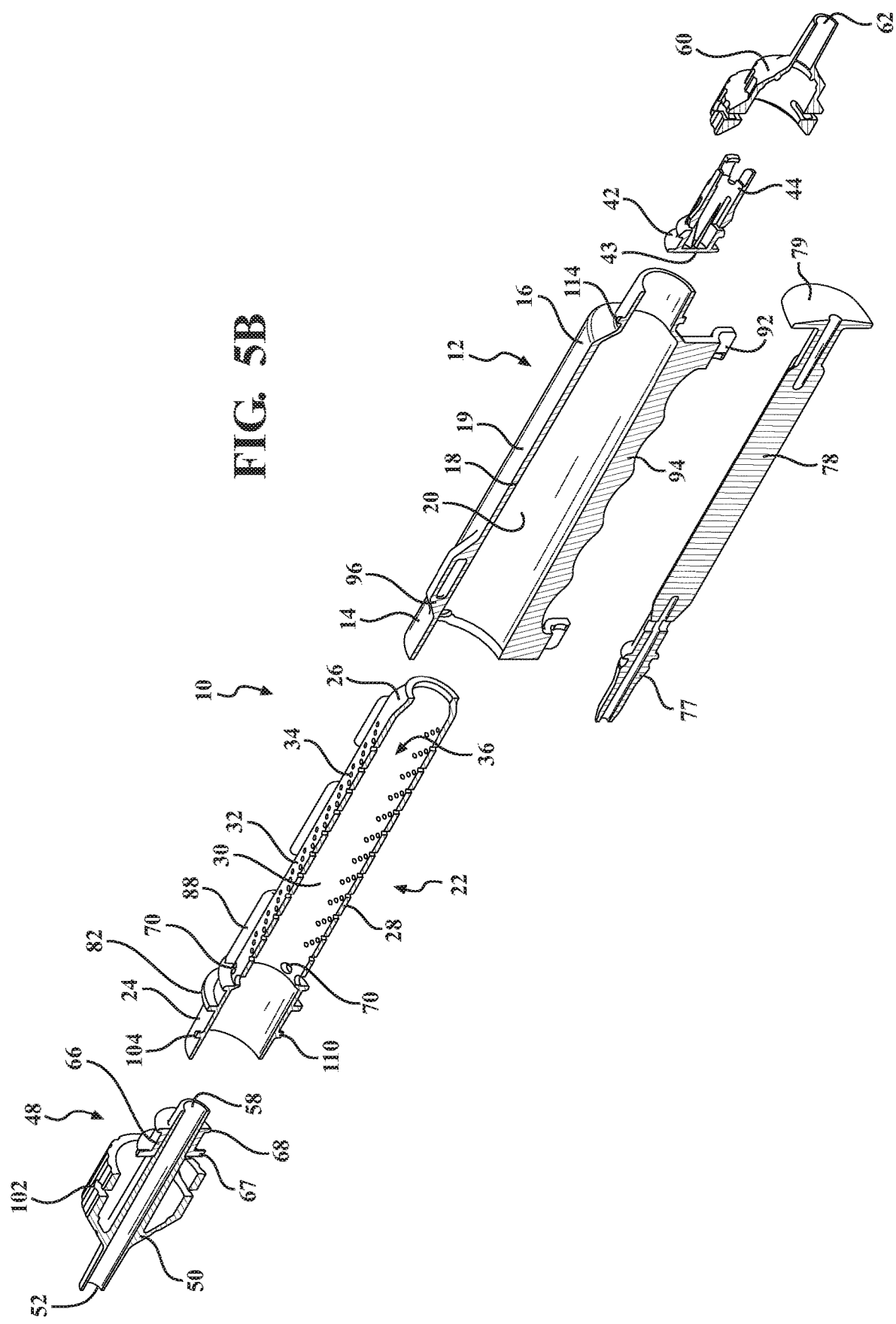

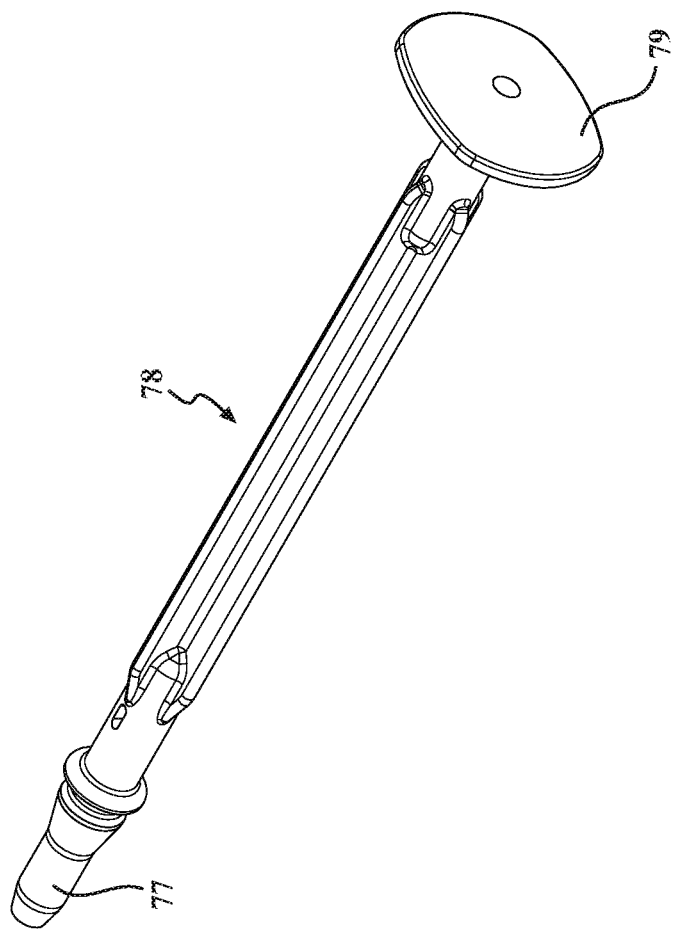
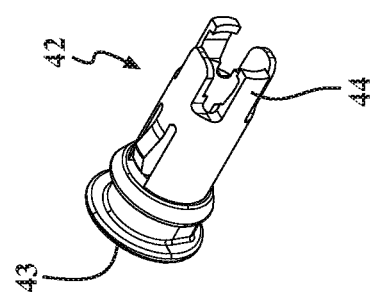
FIG. 6

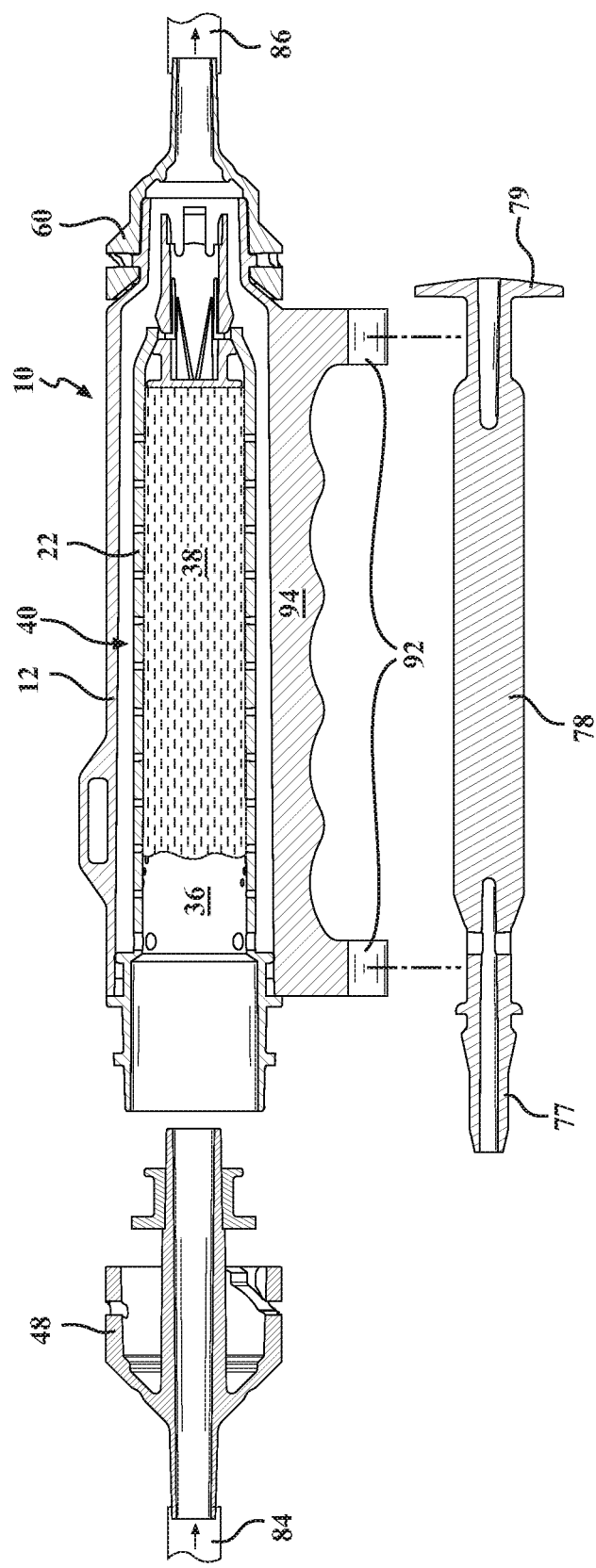

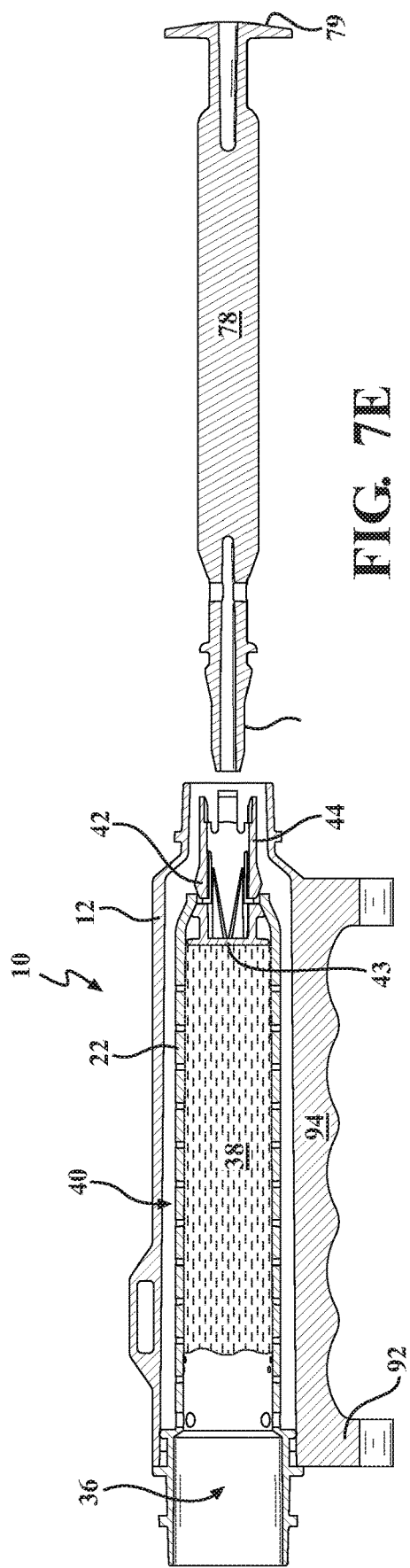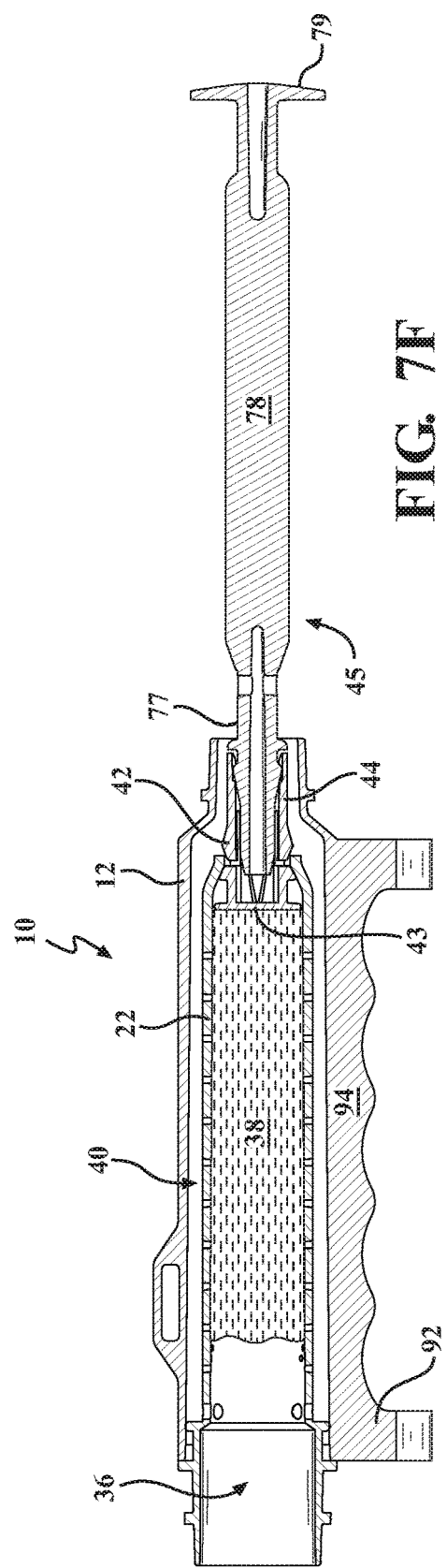

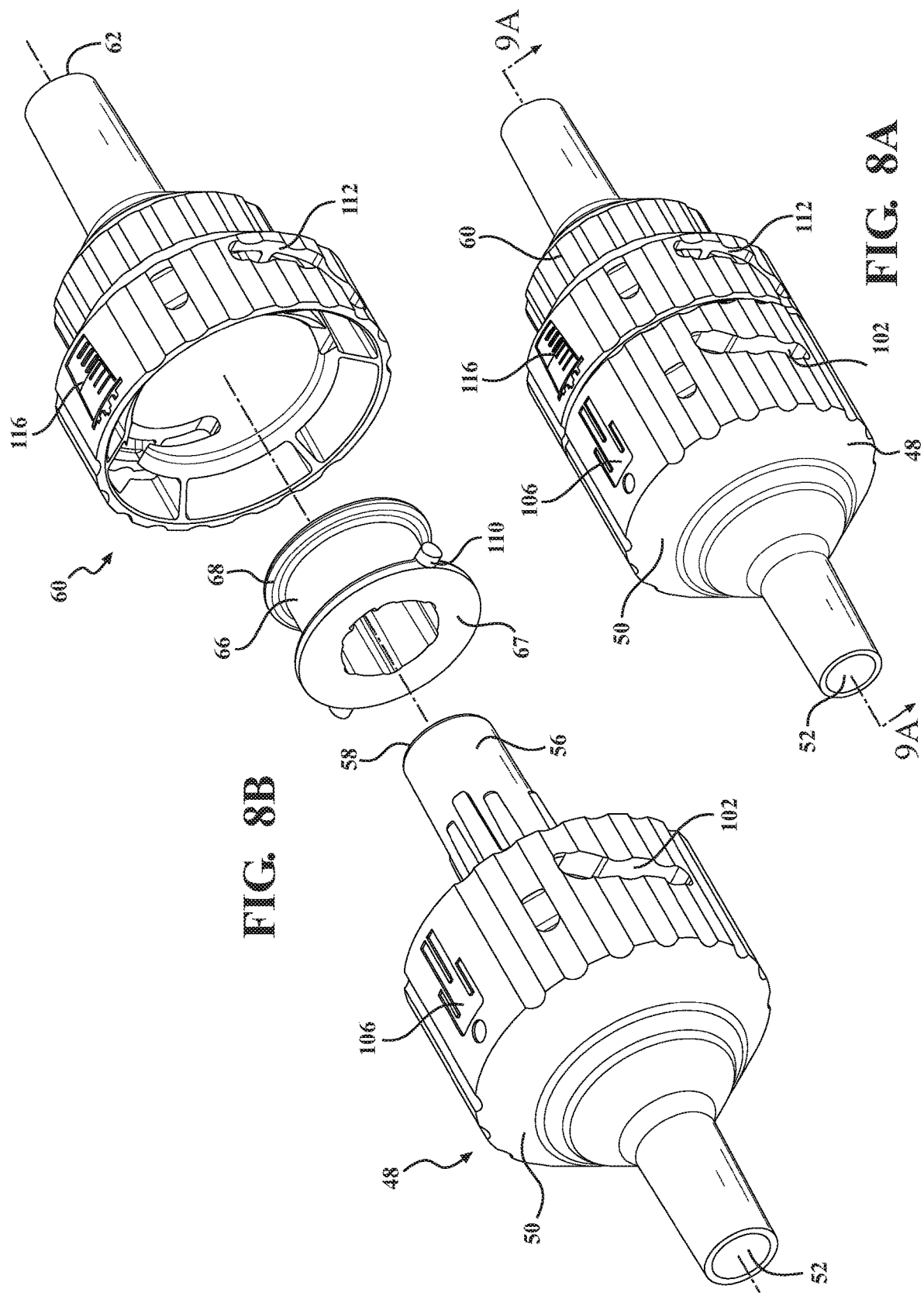

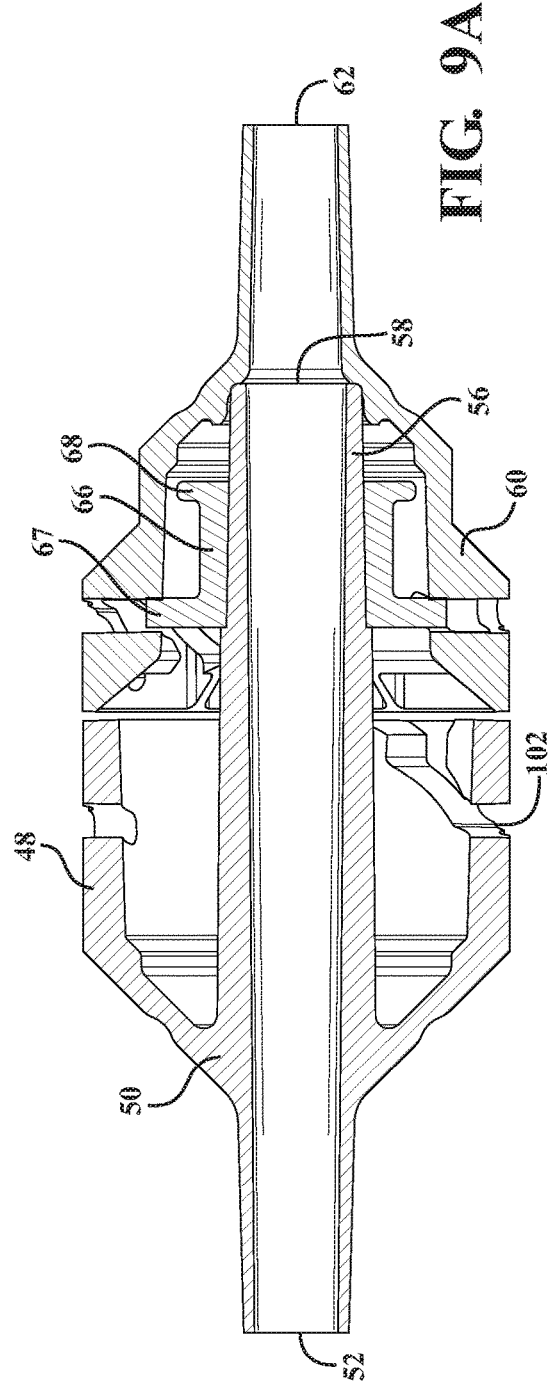
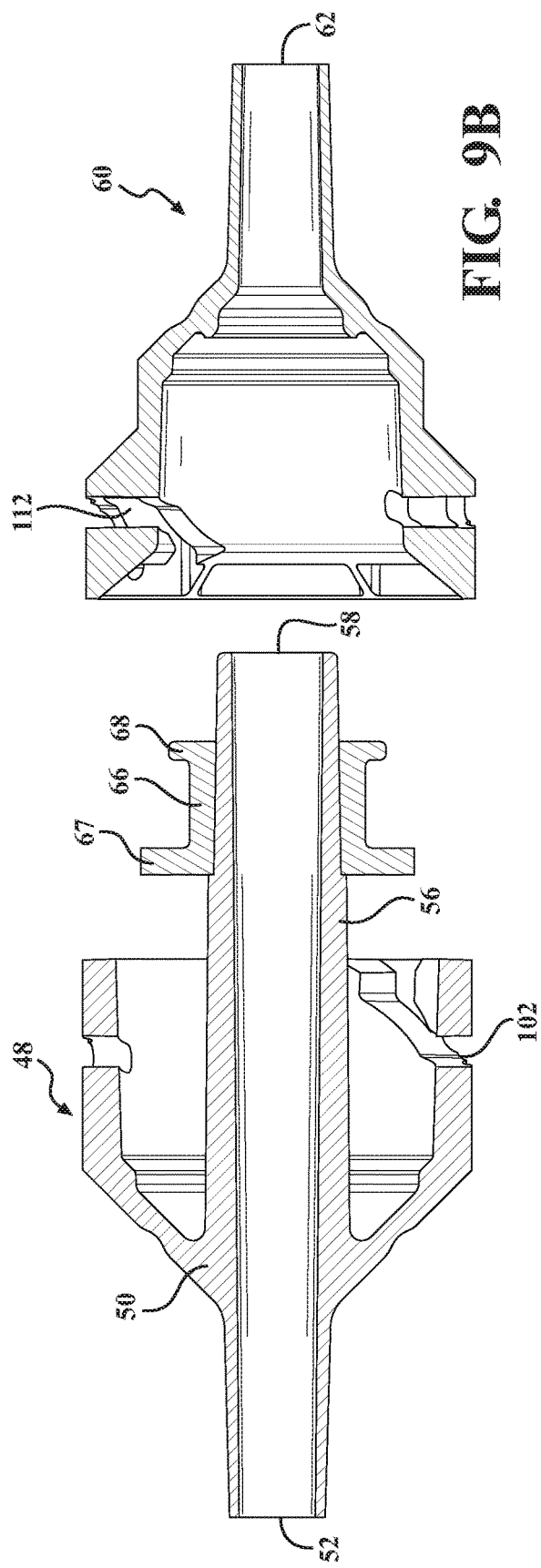

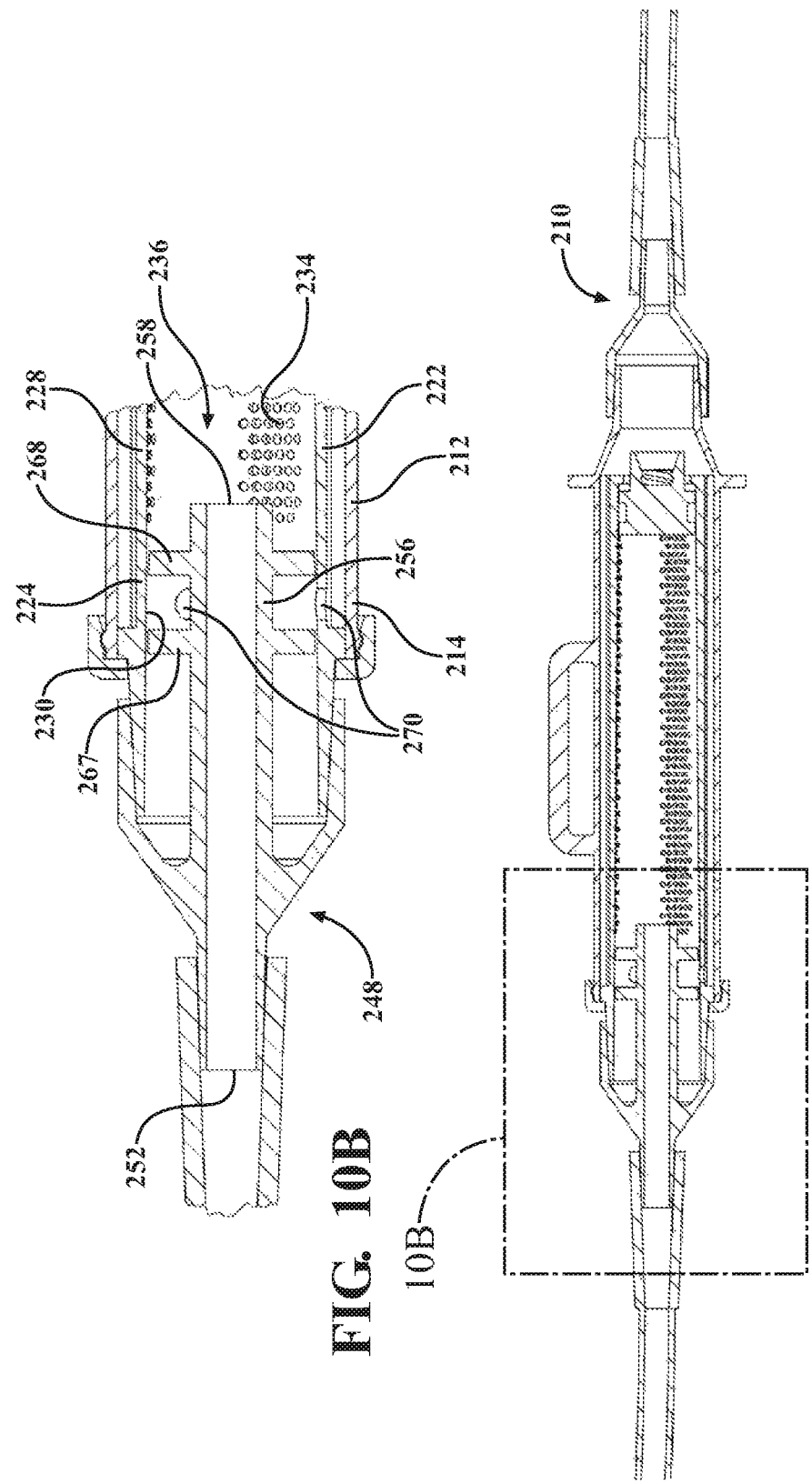

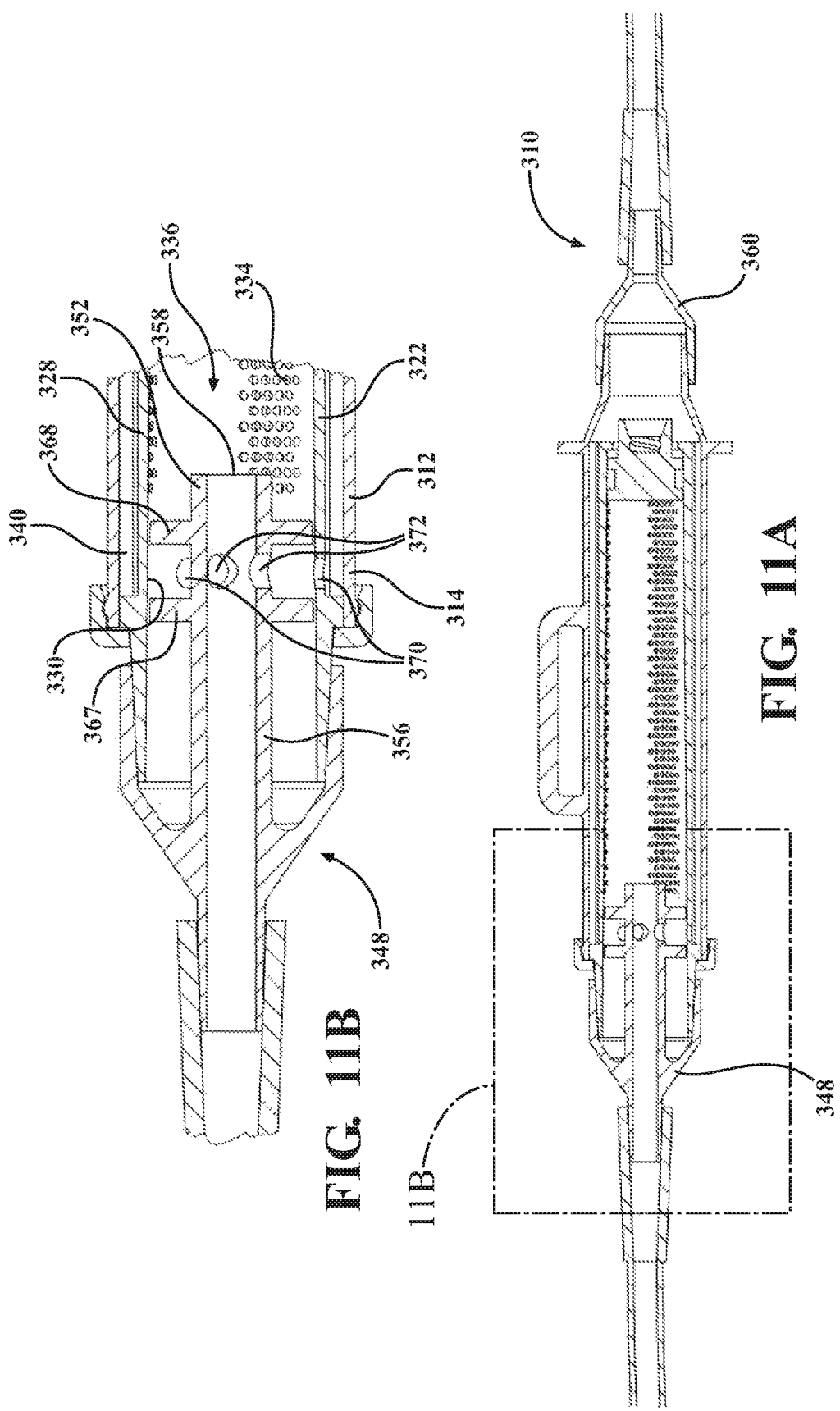

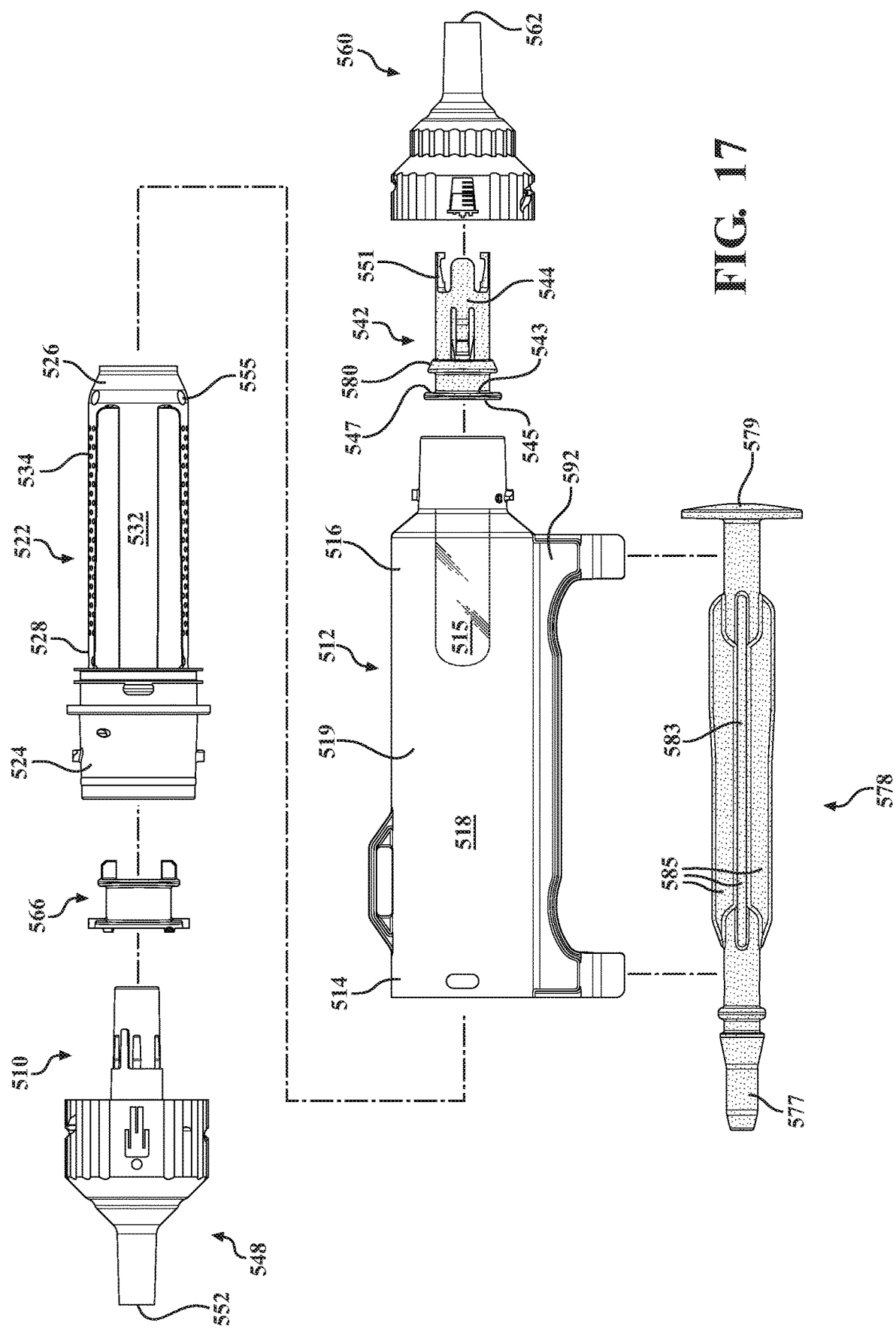

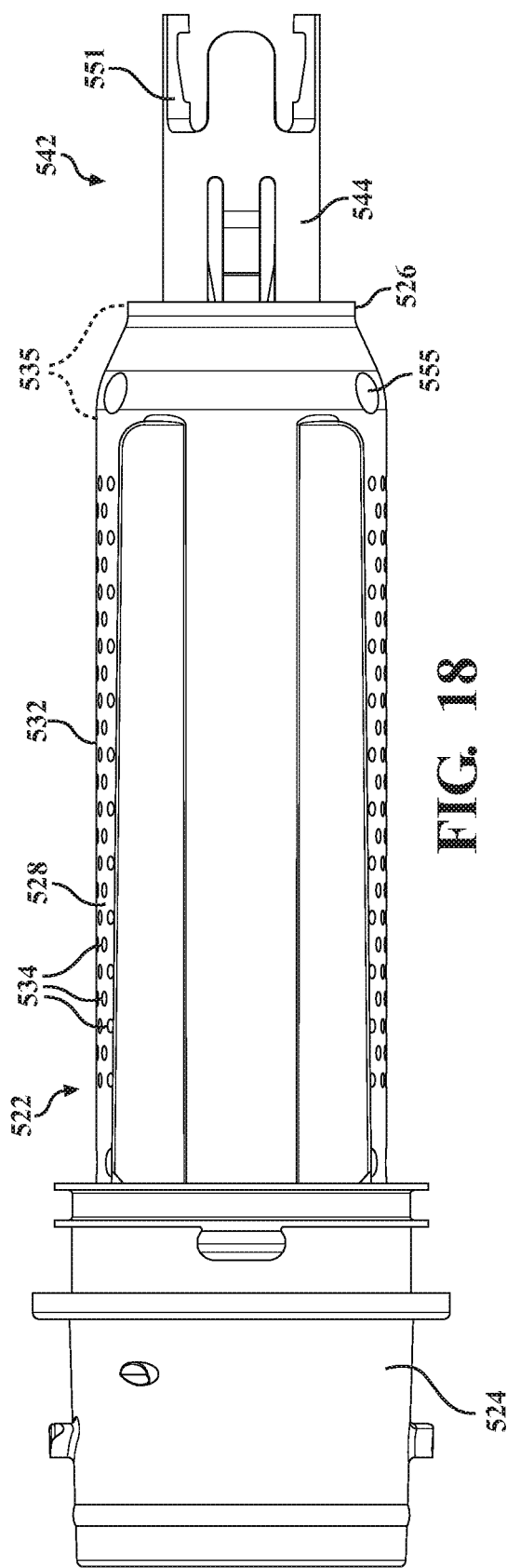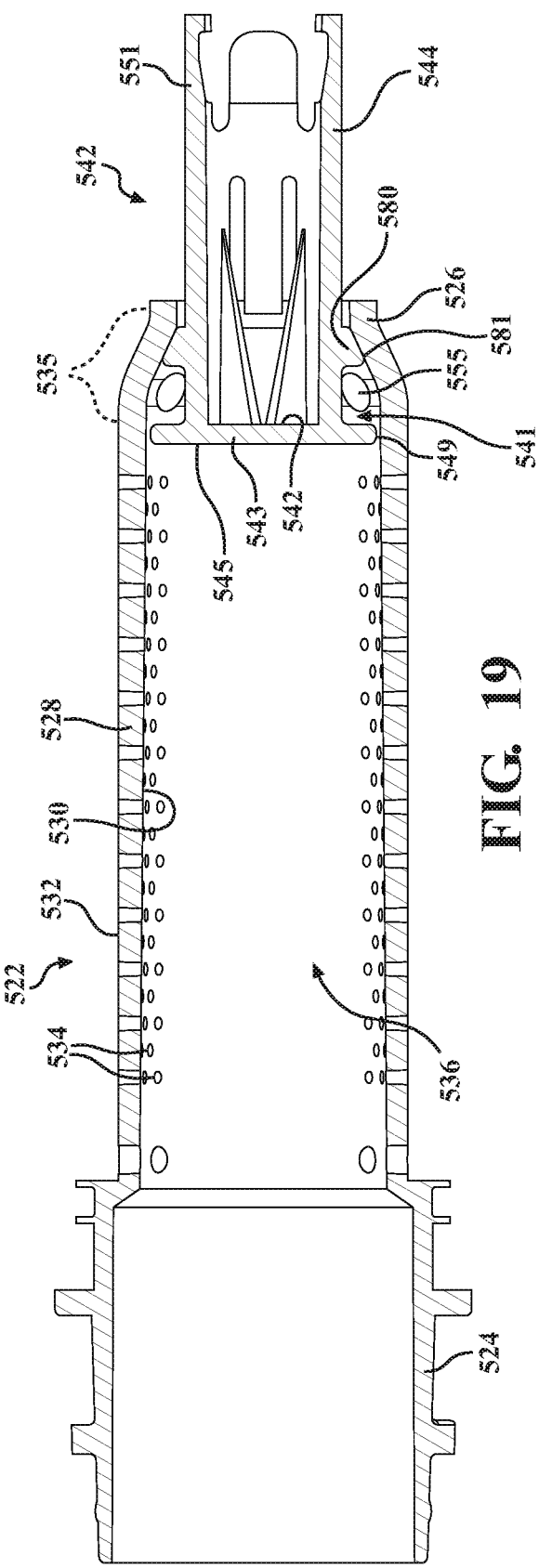

BONE FRAGMENT COLLECTOR AND PROCESSOR

CROSS-REFERENCE TO RELATED APPLICATION

This application is the National Stage of International Application No. PCT/IB2020/061983, filed on Dec. 15, 2020, which claims priority to and all the advantages of U.S. Provisional Patent Application No. 62/949,863, filed on Dec. 18, 2019, the contents of which are incorporated herein by reference.

BACKGROUND

Conventional medical and surgical procedures routinely involve the use of systems and tools which allow surgeons to remove bone. Such systems often generate bone fragments (in many instances with a drill). Once removed, the bone fragments, collectively referred to as bone graft, can be used for reimplantation. In fact, the bone graft is particularly useful in various surgical procedures because it can be used to bridge gaps between bone segments and act as a scaffold for bone growth and subsequent bone fusion.

In some surgical procedures, bone fragments are, as a matter of course, necessarily generated, harvested, and used as bone graft all in the same procedure. For example, spinal procedures (e.g. spinal fusion) require the drilling and removal of various spinal bone, and the subsequent use of bone graft. As another example, joint reconstruction and revision procedures require the drilling and removal of various bone, and the subsequent use of bone graft.

In other surgical procedures, the bone fragments may be intentionally harvested, sometimes from bones in another area of the body, for use in the procedure that requires bone graft. In yet other procedures, bone graft comprising bone from another patient, a cadaver, or even synthetic bone material can be used. Bone graft comprising natural bone, especially bone harvested from a patient for use on the same patient (typically referred to as auto-graft or autologous bone) is preferred by surgeons because of its osteoconductive, osteoinductive, and osteogenic properties and seen as the gold standard for bone fusion surgeries.

While bone collection and processing systems have generally performed well for their intended use, there remains the need to maximize bone fragment recovery and process the bone fragments in a sterile and efficient manner.

BRIEF DESCRIPTION OF THE DRAWINGS

Advantages of the examples disclosed herein will be readily appreciated as the same becomes better understood after reading the subsequent description taken in connection with the accompanying drawings. It is to be understood that the drawings are purely illustrative and are not necessarily drawn to scale.

FIG. 5B is a cross-sectional view of the exploded device illustrated in FIG. 5A.

FIG. 6 is an isolated perspective view of a plunger and a piston of the device of FIG. 1, which are configured to be releasably coupled to one another.

FIG. 7D is a cross-sectional view of the device of FIG. 7C which illustrates the decoupled inlet cap, the filter element with a full collection chamber, and the decoupled plunger which will be subsequently connected to the piston so that force can be applied to the plunger to move the piston from a first position to a second position to discharge the composition from the device.

FIG. 7E is a cross-sectional view of the device of FIG. 7D with a decoupled inlet cap to provide access so that the decoupled plunger can be connected to the piston and force can be applied to the plunger to move the piston from the first position to the second position to discharge the composition from the device.

FIG. 7F is a cross-sectional view of the device of FIG. 7E with the plunger coupled to the piston in the first position.

FIG. 8A is a perspective view of the inlet cap and the outlet cap which were removed from the device and coupled to one another to restore vacuum airflow to the surgical tool.

FIG. 8B is an exploded view of the coupled caps of FIG. 8A.

FIG. 9A is a cross-sectional view of the coupled caps of FIG. 8A along line 9A-9A.

FIG. 9B is an exploded view of the caps of FIG. 9A.

FIG. 10A is a cross-sectional view of an example of the device A-A having an inlet cap which ceases vacuum airflow once a collection chamber is filled with the composition.

FIG. 10B is a close-up view of the distal end of the device of FIG. 10A.

FIG. 11A is a cross-sectional view of another example of the device having an inlet cap with a secondary fluid communication path to maintain vacuum airflow when the collection chamber fills up with the composition.

FIG. 11B is a close-up view of the distal end of the device of FIG. 11A.

FIG. 17 is an exploded view of the device of FIG. 14.

FIG. 18 is an isolated view of a filter element and a piston of the device of FIG. 14.

FIG. 19 is a cross-sectional view of the filter element and the piston of FIG. 18.

DETAILED DESCRIPTION

Figure 1:
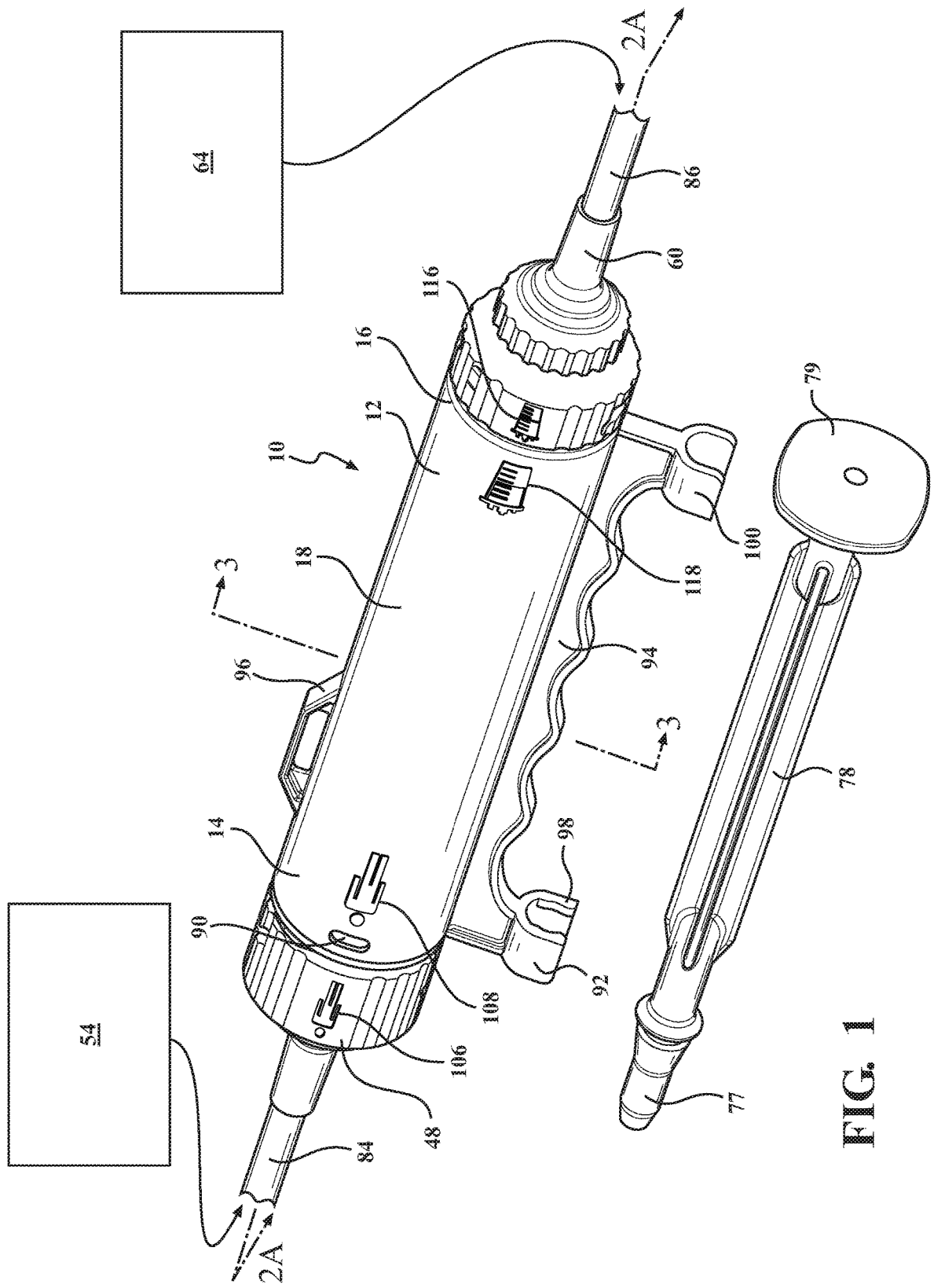
FIG. 1 is perspective view of a device for collecting a composition comprising bone fragments.

With reference to the drawings, where like numerals are used to designate like structures throughout the several views, devices for collecting and processing bone fragments ("the device") are shown throughout the Figures at 10. The device 10 may also be referred to as a "bone dust collector," a "bone fragment collector", or "a bone collecting device." The device 10 of the subject disclosure is configured to collect and process bone fragments in connection with various types of medical and/or surgical procedures. More specifically, the device 10 is configured to process and collect a composition 38 comprising bone fragments and other components ("the composition") from a patient. The composition is shown throughout the Figures as 38. The composition 38 is intended to be broadly construed to encompass all bone components regardless of their form, e.g. bone, tissues such as stem and progenitor cells, etc. For purposes of this disclosure the terms "bone fragments", "bone dust", and "the composition", can be used interchangeably and share the broad construction set forth for the composition 38. Once processed, the composition 38 is typically used to form bone graft. In certain procedures, the composition 38 will include bone fragments, an irrigation solution, such as saline or water, blood, and one or more soft tissue fragments.

In additional aspects, the subject disclosure further provides a system, for use in collecting and processing bone fragments. The system includes a surgical tool 54 configured to harvest the composition 38 and shaped to couple with an intake tube 84. In some examples, the surgical tool 54 is also configured to generate, e.g. grind, cut, shave, or abrade, bone to yield bone fragments. In such examples, the system includes the surgical tool 54 which is configured to both generate bone fragments and harvest, i.e., aspirate, the composition 38. The system may also include the intake tube 84 through which the composition 38 is conveyed from the surgical tool 54 to the device 10 for collecting and processing bone fragments. In a typical example, the composition 38 is aspirated from the patient using the surgical tool 54, which causes the aspirated composition 38 to be collected in the device 10. The vacuum source 64 is in communication with the surgical tool 54 through the device 10 and one or more tubes.

A representative example of the device 10 is illustrated throughout the Figures. As a general overview with reference to FIG. 1, the device 10 includes an inlet cap 48, a housing 12 having a filter element 22 disposed therein, and an outlet cap 60. Generally, the outlet cap 60 is proximally coupled to the device 10, and a vacuum source 64 is coupled to the outlet cap 60 via an outlet tube 86. The outlet cap 60 is in fluid communication with the housing 12 and thus carries a vacuum airflow which aspirates the composition 38 from the patient and causes the subsequent collection of the composition 38 in the device 10. The inlet cap 48 is distally coupled to the device 10, and a surgical tool 54, e.g. a cutting device, is connected to the inlet cap 48 via an intake tube 84. In some examples, the surgical tool 54 generates and subsequently aspirates the composition 38. However, it should be appreciated that the system may include a dedicated handheld aspirator in conjunction with a surgical tool 54, e.g. a cutting tool. In such configurations, the surgical tool 54 illustrated in FIG. 1 is the aspirator, which will aspirate the composition from the surgical site, and the cutting tool (not separately shown) is used to separately generate the composition 38 from the patient.

Figure 2B:
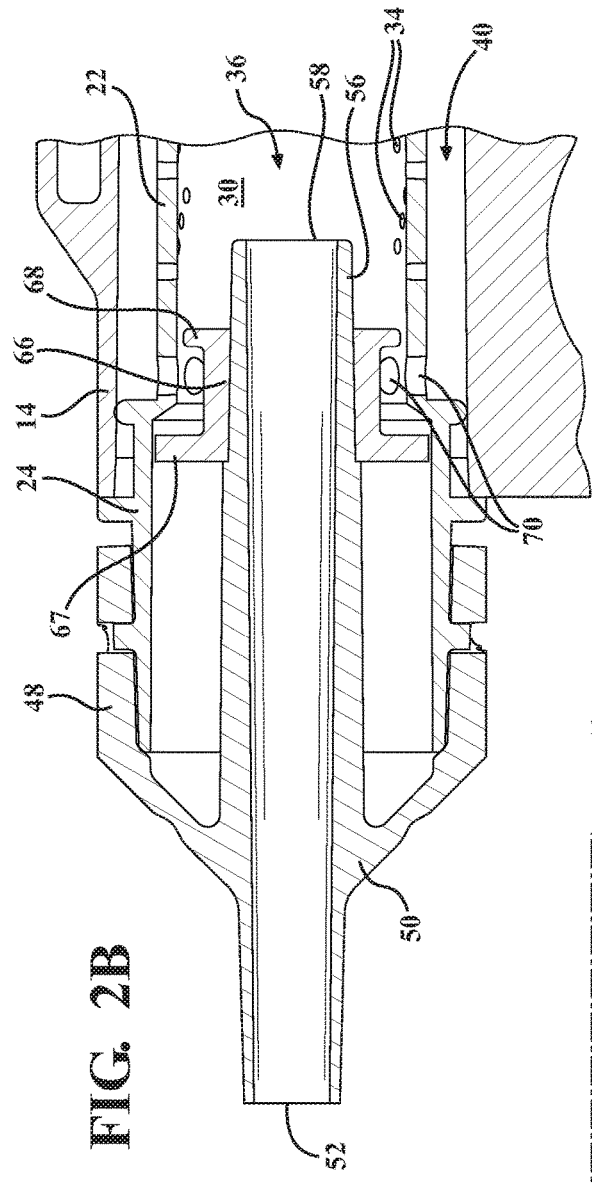
FIG. 2B is an enlarged cross-sectional view of the distal end of device of FIG. 2A.
Figure 2A:
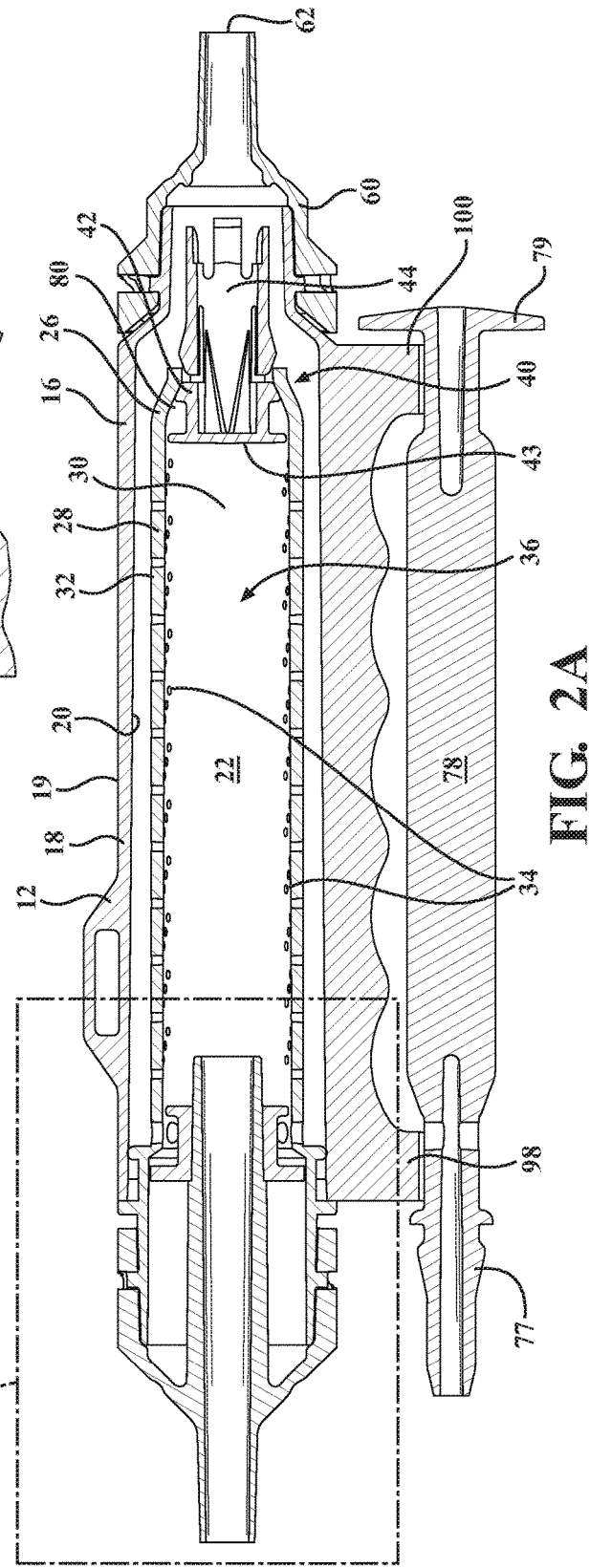
FIG. 2A is a cross-sectional view of the device of FIG. 1 along 2A-2A.

Referring now to FIG. 2A, the inlet cap 48 is in fluid communication with the device 10 and receives the composition 38, which is subsequently deposited/injected into, and collected in a collection chamber 36 which is partially defined by the filter element 22. Once the composition 38 is collected in the collection chamber 36, the inlet and outlet caps 48, 60 can be removed from the housing 12 and/or filter element 22 and the composition 38 can be harvested for use as bone graft. A plunger 78 can then be coupled to the piston 42 and force can be applied to the piston 42 via the plunger 78 to move the piston 42 from a first position 45 to a second position 46 and discharge the composition 38 collected in the collection chamber 36, i.e., the composition 38 can be harvested. Further, once removed, the inlet cap 48 and the outlet cap 60 are configured to be coupled to one another and can thus be coupled together to restore vacuum airflow to the surgical tool 54.

In many examples, the collection chamber has a total volume of from about 5 to about 30, alternatively about 8 to about 25, alternatively from about 10 to about 20, $cm^3$. Such collection chamber volumes allow for collection of an appropriate amount of composition 38, and also facilitate user friendly operation (handling) and harvesting (harvesting with minimal force) of the device 10. In various non-limiting examples, all values and ranges of values including and between those described above are hereby expressly contemplated for use herein.

Referring now to FIGS. 1-12 generally, various examples and aspects of the device 10 are illustrated. Referring now to FIG. 2A, the device of this example includes the housing 12 and the filter element 22 at least partially disposed therein. The housing 12 includes a distal end 14, a proximal end 16, and an outer wall 18 having an outer surface 19 and an inner surface 20 extending between the distal and proximal ends 14, 16. For purposes of the subject disclosure, the distal end 14 is generally closer to the patient, and the proximal end 16 is generally further from the patient, and proximal to the vacuum source 64. In a typical example, the housing 12 is cylindrical in shape and defines a volume. Of course, the housing 12 (and the filter element 22 for that matter) need not be cylindrical—and can thus have a cross-sectional profile other than circular, e.g. can have ovular, elliptical, or polygonal cross-sectional profile. The housing 12 is typically open-ended, unless the inlet and outlet caps 48, 60 are coupled to the respective distal and proximal ends 14, 16. The filter element 22 is partially disposed within the volume. In other words, at least a portion of the filter element 22 is positioned within the lumen of the housing 12.

Figure 4:
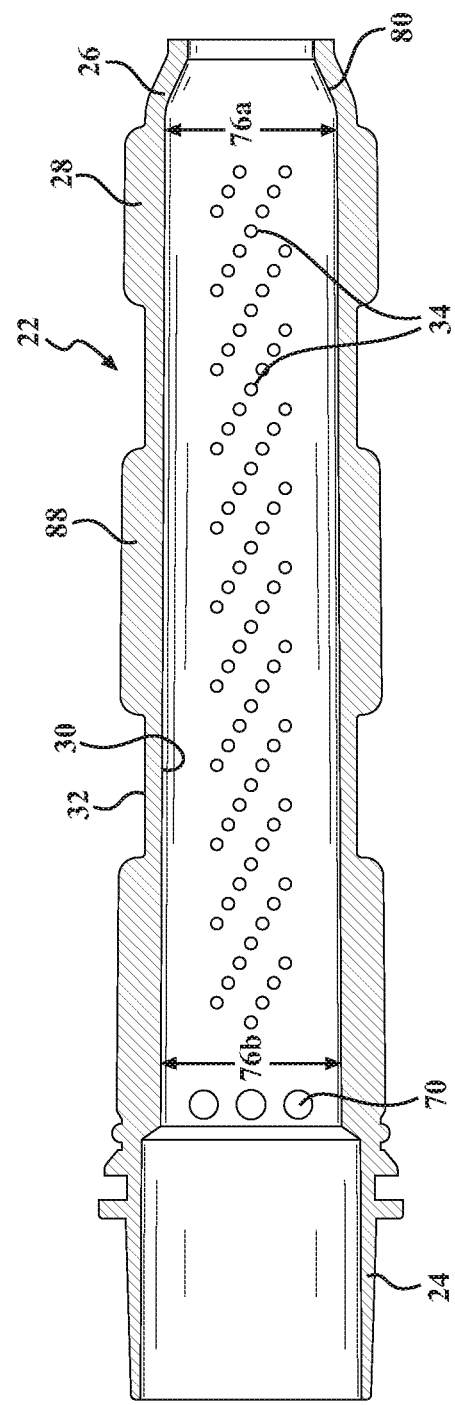
FIG. 4 is an isolated side cross-sectional view of the filter element of the device of FIG. 1 showing a tapered sidewall.

Referring now to FIG. 4, the filter element 22 includes a first end 24, a second end 26, and a sidewall 28 joining the first and second ends 24, 26. The first end 24 is positioned closer to the distal end 14 of the housing 12 than the second end 26, and the second end 26 is positioned closer to the proximal end 16 of the housing 12 than the first end 24. In the configurations shown here, the filter element 22 is open-ended on both the first and second ends 24, 26.

Figure 5A:
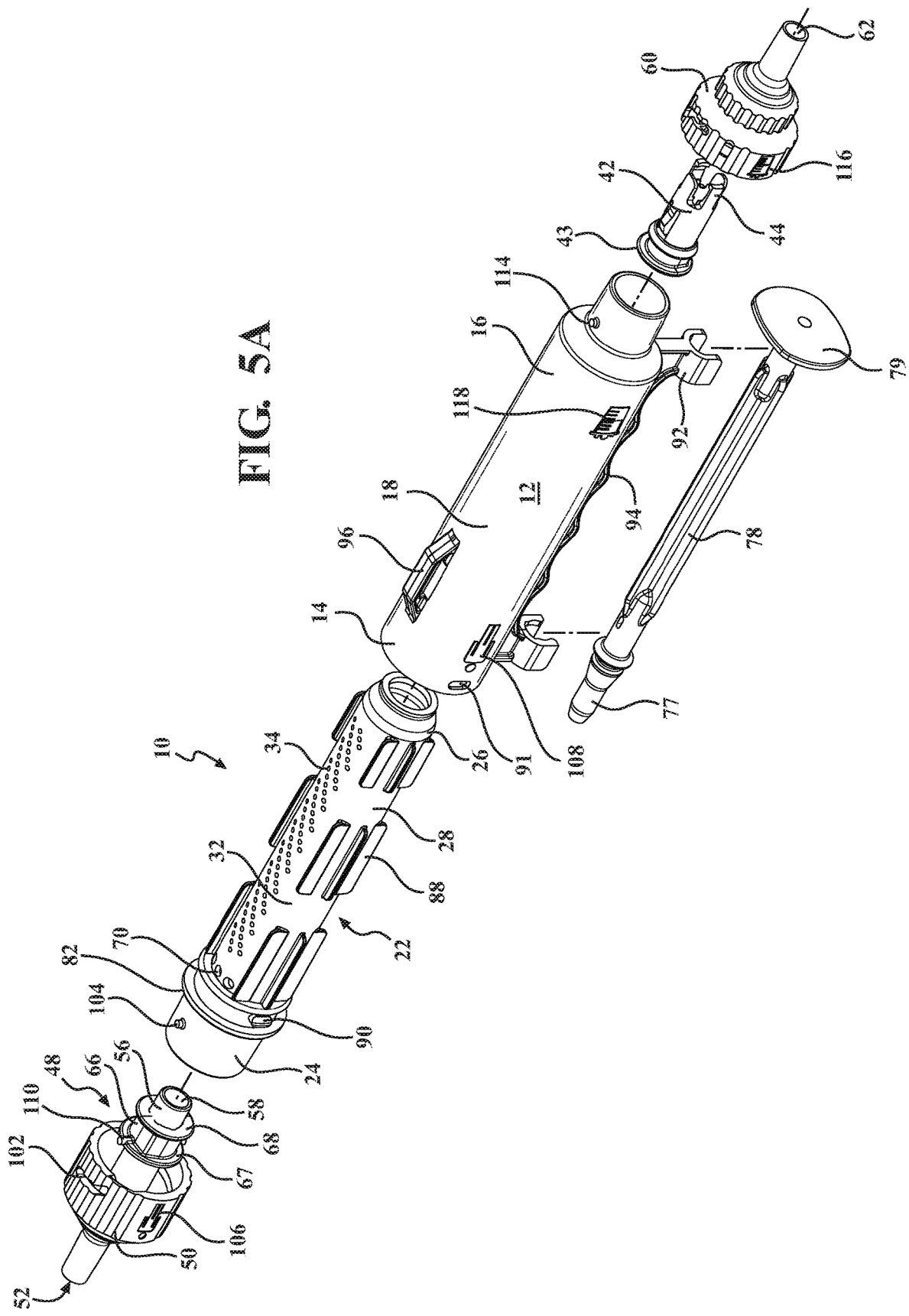
FIG. 5A is an exploded perspective view of the device of FIG. 1.

In the examples shown in the Figures, the filter element 22 is coupled to or secured within the housing 12 via a "snap fit" configuration. In FIG. 5A, one particular example of a "snap fit" configuration is illustrated wherein the first end 24 of the outer peripheral surface 32 of the sidewall 28 of the filter element 22 includes two posts 90 located opposite one another, while the outer wall 18 of the housing 12 includes two corresponding holes 91 into which the two posts 90 are snap fit or secured. Further, the first end 24 of the outer peripheral surface 32 of the sidewall 28 of the filter element 22 includes a collar 82 extending radially around the distal end 14 of the housing 12 for alignment and sealing purposes. Of course, many different mechanisms can be used to couple the filter element 22 to the housing 12, and this is just one non-limiting example.

For example, a collar 82 can be utilized to secure the filter element 22 into the housing 12. In one such example, the collar 82 is L-shaped and has an inner surface that includes a groove extending radially, and the outer wall of the housing 12 includes a corresponding rib extending radially. In such examples, the collar 82 may be integral with the housing 12, the filter element 22, or may be a stand-alone component that joins the housing 12 to the filter element 22. Of course, the housing 12 and the filter element 22 can be sealed mechanically (as described above, interference fit, etc.) or with the use of an elastomeric (e.g. silicone rubber) sealing member. One example of use of the elastomeric sealing member would be the use of a groove and/or a flange (on the housing 12 and/or the filter element 22) in combination with an O-ring which sits between the housing 12 and the filter element 22.

In various examples the housing 12, the filter element 22, the inlet cap 48, and/or the outlet cap 60 are sealed via the elastomeric (e.g. silicone rubber) sealing member(s). One example of use of the elastomeric sealing member would be the use of a groove and/or a flange (on the housing 12 and/or the filter element 22) in combination with an O-ring which sits between the housing 12 and the filter element 22. Another example would be the use of the sealing member on the interior surface of the outlet cap 60 so that the outlet cap 60 has a robust seal when engaged with the device 10 and also a robust seal when engaged with the inlet cap 48 (when used to restore vacuum as described herein).

As is best shown in FIGS. 4, 5A, and 5B, the sidewall 28 of the filter element 22 defines an inner peripheral surface 30 and an outer peripheral surface 32 and has a plurality of apertures 34 therein. The sidewall 28 of the filter element 22 at least partially defines the collection chamber 36 for collection of the composition 38. The outer peripheral surface 32 of the sidewall 28 and the inner surface 20 of the outer wall 18 of the housing 12 are spaced apart from one another to define an exterior radial volume 40. The apertures 34 may take any suitable form, such as perforations, slots, etc.

Figure 3:
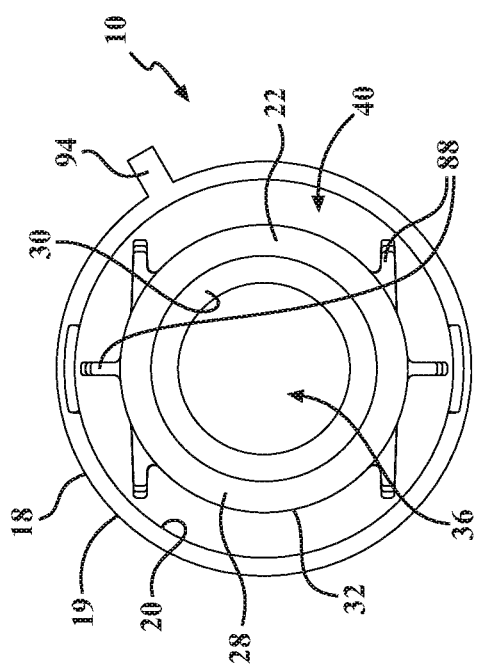
FIG. 3 is a cross-sectional view of the device of FIG. 1 along 3-3.

As is illustrated in FIGS. 3, 4, and 5A, the outer peripheral surface 32 of the sidewall 28 may include one or more ribs 88 extending longitudinally from the first end 24 toward the second end 26 of the filter element 22. The ribs 88 which abut the inner surface 20 of the outer wall 18 of the housing 12 function to strengthen the outer wall 18 and maintain the exterior radial volume 40. The ribs 88 can be continuous or discontinuous. Discontinuous ribs 88 may also be referred to as fins. The example of FIGS. 3, 4, and 5A includes tri-tipped ribs 88. In some examples, where the ribs 88 are continuous, the ribs 88 provide separate fluid channels within the exterior radial volume 40.

Alternatively, in some examples, the ribs 88 may be formed on the inner surface 20 of the housing 12 and can be just as previously described.

In many examples, the sidewall 28 of the filter element 22 also includes at least one bypass hole 70 in fluid communication with the exterior radial volume 40. Of course, more than one hole may be included, and the hole may assume various shapes and sizes. In a typical example, the at least one bypass hole 70 is larger than or has a larger diameter or area than the plurality of apertures 34 in the sidewall 28 of the filter element 22. This at least one bypass hole 70 is positioned so that when the inlet cap 48 is removed, vacuum airflow can be maintained since a fluid communication path can be established through the at least on bypass hole 70, into the exterior radial volume 40 (the volume between the outer peripheral surface 32 of the filter element 22 and the inner surface 20 of the outer wall 18 of the housing 12) and out of the outlet cap 60, without overly drying out the composition 38. It is useful, in certain configurations, to prevent the moisture content of the composition 38 from being lowered too much as maintaining sufficient moisture content has shown to be beneficial for cell viability.

To this end, the filter element 22 is partially within the volume defined by the housing 12. Further, within the filter element 22 is the partially-defined collection chamber 36 (a defined sub-volume) and between the filter element 22 and the housing 12 lies the exterior radial volume 40 (another defined volume). The composition 38 typically follows a primary communication path through the inlet cap 48 and into the collection chamber 36, wherein excess fluid is drawn through the plurality of apertures 34, into the exterior radial volume 40, and out of the outlet cap 60. It should be appreciated that, once the composition 38 is drawn into the collection chamber 36 of the filter element 22, filtrate is drawn through the plurality of apertures 34 in the sidewall 28 of the filter element 22, and out of the outlet cap 60. In so doing, the filter element 22 functions as a filter to further remove filtrate (liquid) components from the composition 38 and thus change the composition 38. As such, the components and properties of the composition 38 (e.g. irrigation solution, blood, excess soft tissue, etc.) taken in by the device 10, the amount of time the composition 38 spends in the filter element 22, the surface area and patterning of the plurality of apertures 34, and the strength of the vacuum all impact the physical characteristics of the "plug" of composition 38 which is formed in the filter element 22.

In some examples, the plurality of apertures 34 collectively open from about 0.5 to about 25, alternatively from about 0.6 to about 10, alternatively from about 0.6 to about 5, alternatively from about 0.7 to about 2, alternatively from about 0.8 to about 1.2, % of a total surface area of the inner peripheral surface 30 of the sidewall 28 of the filter element 22 to optimize hydration (prevent dehydration or excess-hydration) of the composition 38 collected in the collection chamber 36. In some such examples, the plurality of apertures 34 are uniformly spaced about the sidewall 28 of the filter element 22. In other examples, the plurality of apertures 34 are patterned in groups or lines to optimize the hydration of the composition 38 collected in the collection chamber 36. In FIGS. 4, 5A and 5B, one such example of the plurality of apertures 34 is illustrated. In some examples, the apertures can be circular and have a diameter of from about 0.2 to about 2.00, alternatively from about 0.4 to about 1.5, alternatively from about 0.6 to about 1.2, mm. In some examples, the outer peripheral surface 32 of the sidewall 28 may include from about 40 to about 200, alternatively from 80 to about 140, alternatively from about 100 to about 120 apertures 34. The apertures can have shapes other than round as well, e.g. ovular, elliptical, or polygonal shape. In various non-limiting examples, all values and ranges of values including and between those described in the paragraph above are hereby expressly contemplated for use herein.

In some examples, the plurality of apertures 34 are patterned in lines to optimize the hydration of the composition 38 collected in the collection chamber 36. FIG. 4 shows the plurality of apertures 34 arranged in a pattern of diagonal or helical lines in the sidewall 28 of the filter element 22. Of course, the plurality of apertures 34 could be arranged in a pattern of perpendicular lines (not shown in the drawings) in the sidewall 28 of the filter element 22. In such examples, each line can have from about 2-12, alternatively from about 2-4 holes therein. The plurality of apertures 34 (e.g. lines) can be dispersed relatively evenly across, e.g. spread out on the filter element 22, or dispersed as to progressively increase or decrease longitudinally from the first end 24 toward the second end 26 of the filter element 22.

A piston 42 is moveably disposed within the filter element 22. The piston 42 includes a piston element 43, which pushes the plug of the composition 38 out of the collection chamber 36, and a plunger mount 44 opposite the piston element 43 and outside of the collection chamber 36, which cooperates with a corresponding attachment element 77 on the plunger 78 to connect thereto. In a typical example, the plunger mount 44 and the corresponding attachment element 77 are shaped to snap fit with one another. Of course, it should be appreciated that the plunger mount 44 and the corresponding attachment element 77 are shaped in any way suitable to releasably couple to one another.

The piston 42 is movable between a first position 45 and a second position 46. In the first position 45, the piston 42 at least partially defines the collection chamber 36. The piston 42, in conjunction with the sidewall 28 of the filter element 22 defines the end and sidewalls of the collection chamber 36 when the piston 42 is in the first position 45. In other words, the piston 42 functions as a movable end wall of the collection chamber 36. In the first position 45, the piston 42 is located proximate to the second end 26 of the filter element 22, and the volume defined by the collection chamber 36 is at a maximum. In the second position 46, the piston 42 may be located proximate the first end 24 of the filter element 22, and the volume defined by the collection chamber 36 is at a minimum. In some examples, a flange (not shown in the drawings) extends radially about the inner peripheral surface 30 of the sidewall 28 of the filter element 22 at its second end 26 such that the piston 42 abuts the flange when the piston 42 is in the first position 45. In other examples as is shown in FIG. 2A, the piston 42 is profiled such that it includes a radial protrusion that abuts the second end 26 of the sidewall 28 of the filter element 22 which has a tapered portion 80 that is tapered radially inward. The tapered portion 80 allows more space in the exterior radial volume 40 at the proximal end of the device 10 for debris (e.g. accumulated blood clots and other) to be cleared out of the device 10 if accumulation of such debris occurs between the filter element 22 and the housing 12. Plus, the tapered portion 80 allows for a generous lead into the piston 42 when it is in the first position 45 or being assembled into the device 10 so that the piston 42 can be it seated correctly into the filter element 22 and does not get hung up as it can with as flange.

In the example shown in FIG. 2A, the piston 42 includes a front face (radial protrusion) which provides a flat, round surface slideably engaged in the collection chamber 36 to push the composition 38 therethrough. The second radial protrusion acts to provide a second barrier for the composition 38 and stabilizes the piston 42 and plunger 78 thereon as they are pushed through the collection chamber 36 to discharge the composition 38. In various examples, additional distal protrusions (behind the first two protrusions), extending radially around the piston 42 and are used to distally secure the piston 42 within the device 10 during shipping and handling. Such protrusions may extend beyond the clearance radius.

The inlet cap 48 is configured (or shaped) to be releasably coupled to either the distal end 14 of the housing 12 or the first end 24 of the filter element 22. In the examples shown throughout the Figures, the inlet cap 48 is releasably coupled to the first end 24 of the filter element 22. However, it should be appreciated that, in various alternative examples, the inlet cap 48 could be releasably coupled to (or configured to be releasably coupled to) the distal end 14 of the housing 12. The inlet cap 48 includes a body 50, an intake port 52 extending from the body 50 and configured to be coupled to the surgical tool 54, and a spout 56 extending from the body 50 opposite the intake port 52. The spout 56 includes an injection port 58 extending beyond the first end 24 of the filter element 22 and into the collection chamber 36 of the filter element 22. Of course, the inlet cap 48 is configured to receive the composition 38. More specifically, the intake port 52 is typically connected to the surgical tool 54 via the intake tube 84. The composition is drawn through the surgical tool 54, through the intake tube 84, and into the intake port 52 of the inlet cap 48. The composition 38 moves through the body 50 of the inlet cap 48, through the spout 56, and out of the injection port 58 and into the collection chamber 36. Notably, the injection port 58 of the spout 56 extends into the collection chamber 36 at the first end 24 of the filter element 22, and in some examples, into the collection chamber 36 at the first end 24 of the filter element 22 such that the injection port is located proximally (or past) where the apertures 34 are first located on the sidewall 28 of the filter element 22. In other examples, the spout 56 extends into the collection chamber 36 at the first end 24 of the filter element 22 such that the injection port is located distally (or before) where the apertures 34 are first located on the sidewall 28 of the filter element 22. The spout 56 (and a first collar 67 either on the spout 56 or on a vacuum spacer 66) ensures that the composition 38 is delivered into the filter element 22, and also results in a minimal amount of the composition 38 falling out of the device 10 when the inlet cap 48 is removed. The spout 56 helps to project the composition 38 into the filter element 22 towards the piston 42.

In some examples, the spout 56 also helps with the stopping of the vacuum airflow when full. Once the end of the spout 56 is backed up with the composition 38, the flow gradually reduces to below acceptable levels.

The outlet cap 60 is configured (or shaped) to be releasably coupled to either the proximal end 16 of the housing 12 or the second end 26 of the filter element 22. In the examples shown throughout the Figures, the outlet cap 60 is releasably coupled to the proximal end 16 of the housing 12. However, it should be appreciated that, in various alternative examples, the outlet cap 60 could be releasably coupled to the second end 26 of the filter element 22. Further, the outlet cap 60 includes a vacuum port 62 configured to be coupled to a vacuum source 64. Typically, the vacuum port 62 is connected to the vacuum source 64 via the outlet tube 86. As such, the outlet cap 60 is in fluid communication with the device 10.

In FIG. 2B a cross-sectional view along line 2A-2A of the exemplary device of FIG. 1 is illustrated. In the example of FIG. 2B, the inlet cap 48 includes the body 50, the intake port 52 extending from the body 50, and a spout 56 extending from the body 50 opposite the intake port 52. In the example of FIG. 2A, the inlet cap 48 cooperates with the vacuum spacer 66 which is positioned around the outer periphery of the spout 56. In simple terms, the spout 56 is like a finger and the vacuum spacer 66 is like a ring that fits on the finger. Further, an exterior radial surface of the spout 56 is shaped to cooperate with an interior radial surface of the vacuum spacer 66. The vacuum spacer 66 includes the two collars 67, 68. The first collar 67 extends radially around the spout 56 and abuts an inner peripheral surface of the inlet cap 48 when the inlet cap 48 is coupled to the distal end 14 of the housing 12 or the first end 24 of the filter element 22. The second collar 68 extends radially around the spout 56 towards, but does not abut, the inner peripheral surface 30 of the of the sidewall 28 of the filter element 22 when the inlet cap 48 is coupled to the distal end 14 of the housing 12 or the first end 24 of the filter element 22.

In some examples, the inlet cap 48 and spout 56 is molded as one piece and the vacuum spacer 66 including the collars 67, 68 is molded as another piece and then coupled (e.g. press fit, ultrasonically welded, or adhesively bonded (e.g. glued)) to a collar on the spout 56. This design creates an airtight join and simplifies the molding and assembly of the inlet cap 48. That is, the vacuum spacer 66 allows for efficient molding of the inlet cap 48 and efficient assembly of the device 10.

The first collar 67 partially defines the collection chamber 36 and functions to prevent the device 10 from collecting any of the composition 38 substantially distal the injection port 58, which minimizes loss of the composition 38 and makes removal of the inlet cap 48 a neater process. In this example, the device 10 may also include a second collar 68 spaced apart from the first collar 67 and located closer to the intake port 52 than the first collar 67. The second collar 68 extends radially around the injection port 58 towards, but does not abut, the inner peripheral surface 30 of the of the sidewall 28 of the filter element 22. The second collar 68 helps (1) align the inlet cap 48 and the outlet cap 60 when coupled to one another and (2) supports the collar 67 during coupling of the inlet cap 48 and the outlet cap 60 and also once the inlet cap 48 and the outlet cap 60 are coupled.

In some instances, the second collar 68 may also help ensure that the device 10 ceases vacuum once the collection chamber 36 of the filter element 22 is filled with the composition 38, prevents the composition 38 from seeping between the collars 67, 68 and into a secondary fluid communication path once the composition 38 fills the collection chamber 36 of the filter element 22 thus preventing loss of the collected composition 38 through the at least one bypass hole 70 when the inlet cap 48 is connected to the filter element 22.

The secondary fluid communication path runs through at least one bypass hole 70, between the inner surface 20 of the housing 12 and the outer peripheral surface 32 of the filter element 22 and into the exterior radial volume 40, and out of the outlet cap 60.

In the example of FIG. 2A, the at least one bypass hole 70 is located on the sidewall 28 of the filter element 22 such that, when the inlet cap 48 is coupled to the filter element 22, the at least one bypass hole 70 is located between the first and second collars 67, 68 of the vacuum spacer 66. The at least one bypass hole 70 (in the example of FIG. 2A plurality of bypass holes 70) between the collars 67, 68 allows for vacuum airflow to be re-established when the inlet cap 48 is removed from the device 10 filled with the composition 38. That is, the at least one bypass hole 70 provides the secondary fluid communication path once the collection chamber 36 of the filter element 22 of the device is full and the inlet cap is removed. The secondary fluid communication path between the outer peripheral surface 32 of the filter element 22 and the inner surface 20 of the housing 12 is routed around the composition 38 collected in the collection chamber 36 of the filter element 22 to ensure that the composition 38 collected in the collection chamber 36 of the filter element 22 is not overly dried when the inlet cap 48 is removed from the device 10 and the outlet cap 60 is still drawing vacuum. A further benefit of the at least one bypass hole 70 is that any liquids accumulated between the housing 12 and the filter element 22 can be easily drained from the device 10 through the outlet cap 60 with vacuum airflow which is reestablished through the secondary fluid communication path.

It should be appreciated that some examples of this device 10 do not include a vacuum spacer 66, just the two collars 67, 68. In such examples, the first collar 67 extends from and radially around the spout 56 and abuts an inner peripheral surface of the inlet cap 48 when the inlet cap 48 is coupled to the distal end 14 of the housing 12 or the first end 24 of the filter element 22 and the second collar 68 extends from and radially around the spout 56 towards, but does not abut, the inner peripheral surface 30 of the of the sidewall 28 of the filter element 22 when the inlet cap 48 is coupled to the distal end 14 of the housing 12 or the first end 24 of the filter element 22.

FIGS. 10A and B and 11A and B illustrate two different examples of the device 10 that does not include the vacuum spacer 66, just the two collars 67, 68. FIGS. 10A and B illustrate an example of the device 210 having an inlet cap 248 that that does not include the vacuum spacer 66 and that ceases to allow vacuum air flow once the collection chamber 236 is filled with the composition 38. In contrast, FIGS. 11A and B illustrates an example of the device 310 having an inlet cap 348 that does not include the vacuum spacer 66 and that allows for the overflow of the composition 38 and maintains vacuum airflow when the collection chamber 336 fills up with the composition 38.

Referring now specifically to the example of FIG. 10B, the device 210 illustrated includes the inlet cap 248. The inlet cap may include the first collar 267 extending radially around the spout 256 and abutting the inner peripheral surface 230 of the sidewall 228 of the filter element 222 when the inlet cap 248 is coupled to the distal end 214 of the housing 212 or the first end 224 of the filter element 222. This first collar 267 partially defines the collection chamber 236 and functions to prevent the device 10 from collecting any of the composition 38 substantially distal the exit of an injection port 258, which minimizes loss of the composition 38 and makes removal of the inlet cap 248 a neater process. In this example, the device 210 may also include the second collar 268 spaced apart from the first collar 267 and located closer to the intake port 252 than the first collar 267. Like the first collar 267, the second collar 268 also extends radially around the spout 256 and abuts the inner peripheral surface 230 of the sidewall 228 of the filter element 222 when the inlet cap 248 is coupled to the distal end 214 of the housing 212 or the first end 224 of the filter element 222. In the example of FIG. 10, the at least one bypass hole 270 is located on the sidewall 228 of the filter element 222 such that, when the inlet cap 248 is coupled to the filter element 222, the at least one bypass hole 270 is located between the first and second collars 267, 268 of the spout 256. The at least one bypass hole 270 located on the sidewall 228 of the filter element 222 is different than a plurality of apertures 234 also found on the sidewall 228 of the filter element 222. As such, the at least one bypass hole 270 does not function until the inlet cap 248 is decoupled and the ceases to allow vacuum air flow once the collection chamber 236 is filled with the composition 38.

Referring now specifically to the example of FIG. 11B, the device 310 illustrated includes the inlet cap 348 having the first and second collars 367, 368 which extend radially around the spout 356 and abut the inner peripheral surface 330 of the sidewall 328 of the filter element 322 when the inlet cap 348 is coupled to the distal end 314 of the housing 312. In the example of FIG. 11, the at least one bypass hole 370 is located on the sidewall 328 of the filter element 322 such that, when the inlet cap 348 is coupled to the filter element 322, the at least one bypass hole 370 is located between the first and second collars 367, 368 of the spout 352. The at least one bypass hole 370 located on the sidewall 328 of the filter element 322 is different than a plurality of apertures 334 also found on the sidewall 328 of the filter element 322. Further, the injection port 358 of the spout 356 includes at least one corresponding bypass hole 372, wherein the corresponding bypass hole 372 is located between the first and second collars 367, 368 of the spout 356 and thus in communication with the at least one bypass hole 370 located on the sidewall 328 of the filter element 322 when the inlet cap 348 is coupled to the filter element 322 such that a secondary fluid communication path is provided. The overflow fluid path runs through wherein the corresponding bypass hole 372, between the first and second collars 367, 368, the at least one bypass hole 370, through the corresponding at least one bypass hole 372, into the exterior radial volume 340, and out of the outlet cap 360 and thus provides an over flow path for the composition 38 and maintains vacuum airflow when the filter element 322 fills up with the composition 38. As such, the inlet cap 348 is designed to maintain vacuum airflow once the collection chamber 336 is filled with the composition 38.

It should be appreciated that when the device 10 includes a vacuum spacer 66 some examples can include a vacuum spacer which includes a third bypass hole to allow the device 10 to maintain vacuum airflow once the collection chamber 36 is filled with the composition 38.

FIG. 3 is a cross-sectional view of the device 10 of FIG. 1 along 3-3. FIG. 4 is an isolated cross-sectional view of the filter element 22 having a sidewall 28 which is tapered such that a diameter of the collection chamber 36 and cross-sectional area of the collection chamber 36 in a longitudinal direction of the filter element 22 increases as the sidewall 28 extends from the second end 26 towards the first end 24 of the filter element 22. Still referring to FIG. 4, both the tapering of the sidewall 28, and the decrease in the diameter and cross-sectional area of the collection chamber 36 is shown. For example, the diameter 76a of the collection chamber 36 at the second end 26 of the filter element 22 is less than the diameter 76b of the collection chamber 36 at the first end 24 of the filter element 22. In the example of FIG. 4, the tapering is accomplished via decreasing thickness of the sidewall 28 as it extends form the second end 26 to the first end 24 of the filter element 22. In such examples, force required to move the piston 42 from the first position 45 to the second position 46 when the collection chamber 36 is filled with the composition 38 is minimized. That is, the tapered sidewall 28 facilitates the discharge of the composition 38 from the collection chamber 36 of the filter element 22. In other words, the increasing cross-sectional area makes the movement of the piston 42 from the first position 45 to the second position 46 easy, such that less force needs to be applied through the plunger 78 and jamming of the device 10 does not occur. Further, as a secondary benefit, the device optimizes the hydration of the "plug" of the composition 38 in the collection chamber 36 which also makes discharge easier because the composition 38 does not flow around or enter into a gap between the face of the piston 42 and the sidewall 28 of the filter element 22, where the gap in size increases as the piston 42 moves from the first position 45 to the second position 46. Furthermore, the composition 38 is hydrated sufficiently, making the effective size of the bone fragments large enough in at least one dimension such that the composition 38 does not flow around or enter into a gap between the face of the piston 42 and the sidewall 28 of the filter element 22, where the gap in size increases as the piston 42 moves from the first position 45 to the second position 46. It should be appreciated that the cross-sectional area of the piston 42 and/or cross-sectional of the filter element 22 may be adjusted such that the size of the gap is small enough to prevent bone fragments from moving therethrough.

FIG. 5A is an exploded perspective view of the device 10 of FIG. 1 and FIG. 5B is an exploded cross-sectional view of the device 10 of FIG. 5A. FIG. 5B, also illustrates the tapered sidewall 28 of the filter element 22 of the example of FIG. 1.

The device 10 includes a plunger 78 configured to be releasably coupled to the piston 42 to move the piston 42 between the first and second positions 45, 46. The plunger 78 includes the corresponding attachment element 77 and also a press pad 79. In FIG. 6, an isolated perspective view of a plunger 78 and a piston 42 of the device of FIG. 1, which are configured to be releasably coupled via a "snap fit" to one another, are illustrated.

In some examples, the corresponding attachment element 77 of the plunger 78 and a piston attachment element of the plunger mount 44 are shaped to releasably couple to one another via various interfaces including, but not limited to, a threadable interface, such as with a bayonet joint, a "snap fit" interface, etc.

Figure 12:
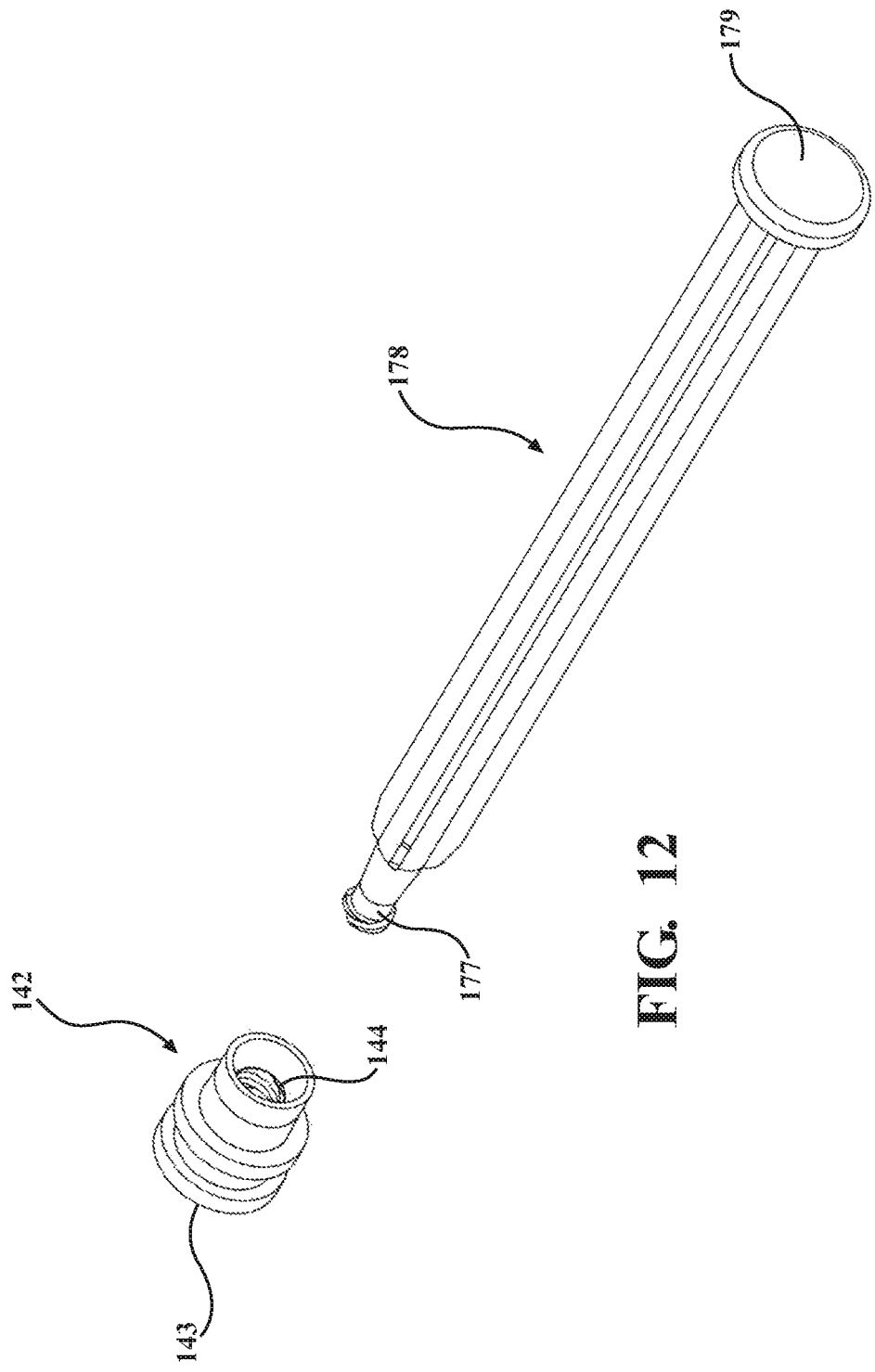
FIG. 12 is an isolated perspective view of an alternative example of a plunger and a piston, which are configured to be releasably coupled to one another.

In FIG. 12, a plunger 178 and a piston 142, which are configured to be threadably coupled to one another is illustrated. In the example of FIG. 12, a corresponding attachment element 177 of the plunger 178 and a plunger mount 144 of the piston 142 are threaded. Once coupled, the press pad 179 of the plunger 178 can be pressed to move the piston 142 such that the front face 143 pushes a plug of the composition 38 out of the device 10.

In various examples, once the collection chamber 36 is full of the composition 38, and the inlet and outlet caps 48, 60 are removed, the plunger 78 can be coupled to the piston 42. Force can be applied to the plunger 78 to move the piston 42 from the first position 45 to the second position 46 to discharge the composition 38 from the collection chamber 36 of the filter element 22. The plunger 78 can also be used to move the piston 42 back to the first position 45, i.e., retract the position, and then be decoupled from the piston 42. Once the plunger 78 is decoupled from the piston 42, the caps 48, 60 can be removed and the process can be repeated to harvest and discharge more of the composition 38.

In many examples, the inlet cap 48 and the outlet cap 60 are configured to be coupled to one another such that after the composition 38 is acquired through the intake port 52 and collected in the collection chamber 36 and the inlet cap 48 and the outlet cap 60 have been removed from the filter element 22 and/or the housing 12 to harvest the composition 38, the inlet cap 48 and the outlet cap 60 can be coupled to one another to restore vacuum airflow to the surgical tool 54. FIGS. 8A and 8B and 9A and 9B illustrate the coupling of the inlet cap 48 and the outlet cap 60.

Referring now to FIGS. 8A and 8B, the vacuum spacer 66 includes the first and second collars 67, 68, as well as a J-notch post 110. Referring now to FIGS. 9A and 9B, the inlet cap 48 and the outlet cap 60 can be coupled by inserting the J-notch post 110 of the vacuum spacer 66 on the spout 56 of the inlet cap 48 into a J-notch 112 of the outlet cap 60 and rotating the inlet cap 48 to releasably couple the inlet cap 48 to the outlet cap 60, an indicium 116 on the outlet cap 60 and the indicium 106 on the inlet cap 48 line-up to indicate that the outlet cap 60 and the inlet cap 48 are fully engaged. The vacuum spacer 66 ensures that when the inlet and outlet caps 48, 60 are coupled to one another to restore vacuum airflow there is a seal between the inlet and outlet caps 48, 60 to prevent the accumulation of fluid therebetween, while the spout 56 provides a bridging lumen between the inlet and outlet caps 48, 60. It should be appreciated that in various examples, the inlet cap 48 (the body 50 and/or the spout 56) may also include the first collar 67, the second collar 68, and/or a J-notch post 110. For example, the first and second collars 67, 68 could extend radially around the spout 56 and the J-notch post 110 could also be located on the spout 56 or body 50.

As described above, the inlet cap 48 and the outlet cap 60 are configured (or shaped) to be releasably coupled to the filter element 22 and/or the housing 12. The inlet and outlet caps 48, 60 can be coupled to the device 10 via mechanical know in the art (e.g. snap fit, J-notch, and other mechanical couplings.

Referring now to FIG. 1, the inlet cap 48 is releasably coupled to the first end 24 of the filter element 22. A J-notch post 104 on the first end of the filter element 22 cooperates with a J-notch 102 on the inlet cap 48 to couple the inlet cap 48 to the device 10. As is shown in FIG. 1, when the inlet cap 48 is fully engaged with the device 10, an indicium 106 on the inlet cap 48 lines-up with an indicium 108 on the housing 12 to indicate that the inlet cap 48 is fully engaged with the device 10.

Figure 13:
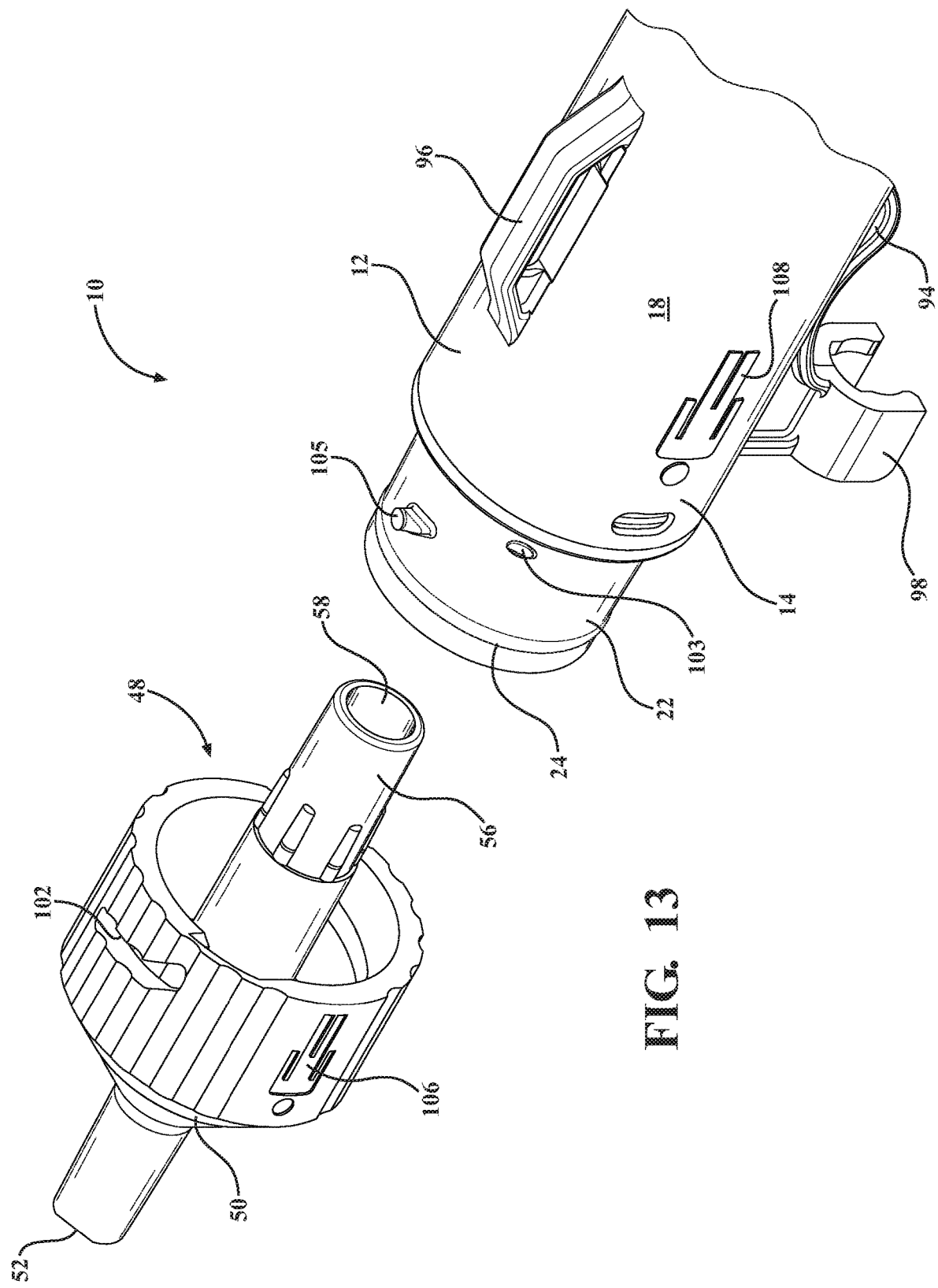
FIG. 13 is a perspective view of the device including an inlet cap which can be releasably coupled to the first end of the filter element.

Referring now to FIG. 13, an example of the device 10 with an alternative inlet cap 48 is releasably coupled to the first end 24 of the filter element 22. In the example of FIG. 13, a "tear drop" shaped J-notch post 105 on the first end 24 of the filter element 22 is shown. The J-notch post 105 provides more contact with the J-notch 102 and more robust engagement/coupling between the inlet cap 48 and the filter element 22. In various examples, the device includes J-notch posts of various cross-sectional profiles e.g. round, ovular, elliptical, polygonal, or tear-drop shaped as shown in FIG. 13. Further, in the example device 10 of FIG. 13 a friction button 103 on the first end 24 of the filter element 22 is shown. When the inlet cap 48 is engaged with the filter element 22 the friction button 103 sits at a mouth of the J-notch 102 to prevent the inlet cap 48 from moving, thereby ensuring that the inlet cap 48 maintains full engagement with the device 10 (i.e. is not loosened during shipping and collection). The "tear drop" shaped J-notch post 105 on the first end 24 of the filter element 22 is also effective at keeping the inlet cap 48 coupled tightly to the filter element 22 during shipping and collection.

Referring back to FIG. 1, the outlet cap 60 is releasably coupled to the proximal end 16 of the housing 12. The outlet cap 60 has the J-notch 112 therein and the proximal end of the outer wall 18 of the housing 12 has a J-notch post 114 thereon. Referring again to FIG. 1, when the outlet cap 60 is fully engaged with the device 10 the indicium 116 on the outlet cap 60 and an indicium 118 on the housing 12 line-up to indicate that the outlet cap 60 and the housing 12 are fully engaged.

A method of collecting and processing bone fragments with the device 10 is also disclosed herein. The method utilizes various examples of the device 10 as described above and includes the steps of: providing the device 10; acquiring the composition 38 through the inlet cap 48; collecting the composition 38 in the filter element 22; decoupling the inlet cap 48 from the housing 12 or the filter element 22; decoupling the outlet cap 60 from the housing 12; applying a force in a first direction to move the piston 42 from the first position 45 to the second position 46 to discharge the composition 38 from the filter element 22; and applying a force in a second direction so that the device 10 can be used to harvest more of the composition 38.

FIGS. 7A-7G illustrate various steps which may be included in the method of collecting and processing bone fragments with the device 10.

Figure 7A:
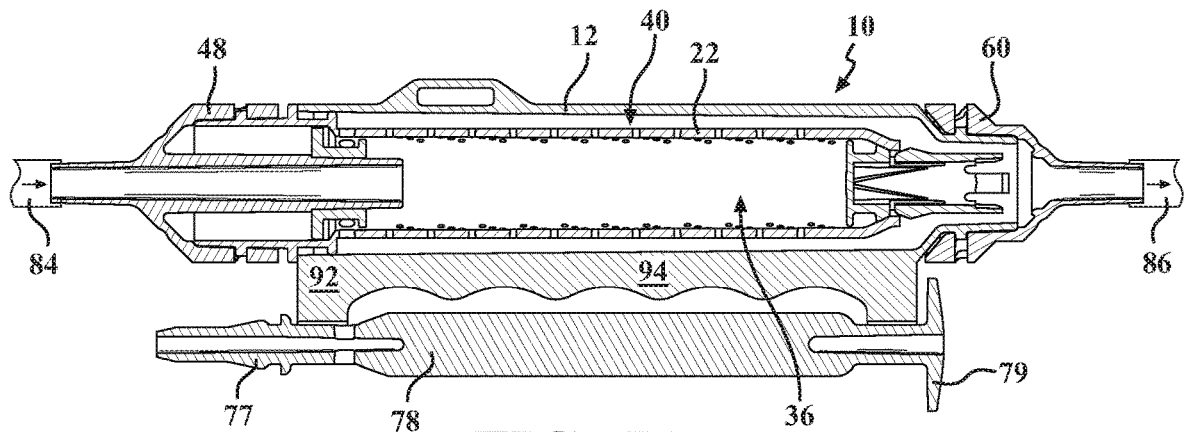
FIG. 7A is a cross-sectional view of the device of FIG. 1 which illustrates the step of acquiring the composition comprising bone fragments through the inlet cap of FIG. 2B.
Figure 7B:
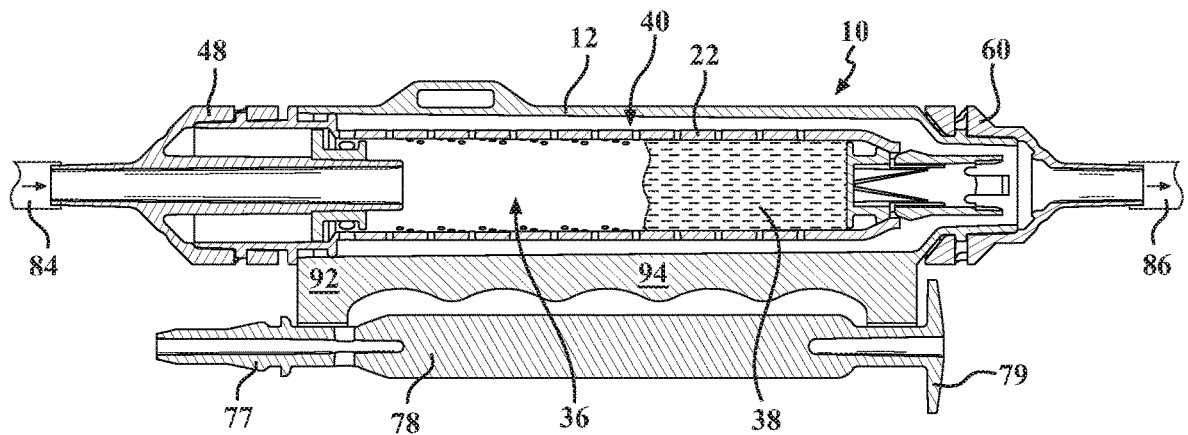
FIG. 7B a cross-sectional view of the device of FIG. 7A which further illustrates the step of acquiring the composition comprising bone fragments wherein a collection chamber is about half full.
Figure 7C:
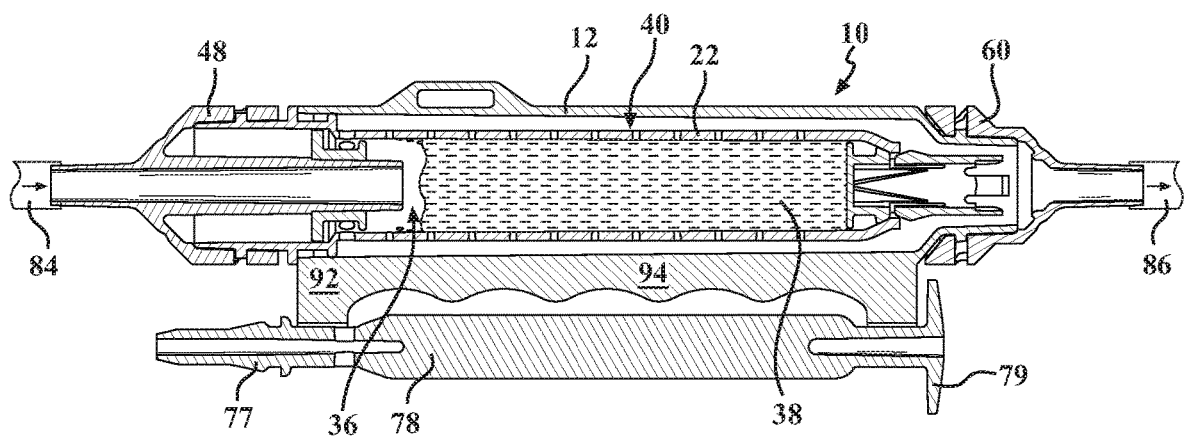
FIG. 7C a cross-sectional view of the device of FIG. 7B which further illustrates the step of acquiring the composition comprising bone fragments wherein a collection chamber is just about full.

FIGS. 7A-7C provide a cross-sectional view of the device 10 of FIG. 1 during the step of acquiring the composition 38 through the inlet cap 48. In FIG. 7A a cross-sectional view of the device of FIG. 1 which illustrates the onset of collection of the composition 38. In FIG. 7B, the composition 38 has started to collect in the collection chamber 36 of the device. FIG. 7C illustrates the final stages of collection wherein the collection chamber 36 is just about full of the composition 38 comprising bone fragments.

FIG. 7D is a cross-sectional view of the device 10 of FIG. 7C which illustrates the decoupled inlet cap 48, the filter element 22 within the housing 12 filled with the composition 38 now filtered, the outlet cap 60 coupled to the housing 12, and the decoupled plunger 78 which will be subsequently connected to the piston 42 so that force can be applied to the plunger 78 to move the piston 42 from the first position 45 to the second position 46 to discharge the composition 38 from the device 10. In FIG. 8, the step of decoupling the inlet cap 48 from the filter element 22 has occurred, and the step of decoupling the outlet cap 60 from the housing 12 will subsequently occur so that the piston 42 can be moved from the first position 45 to the second position 46 to discharge the composition 38 from the device 10.

Figure 7G:
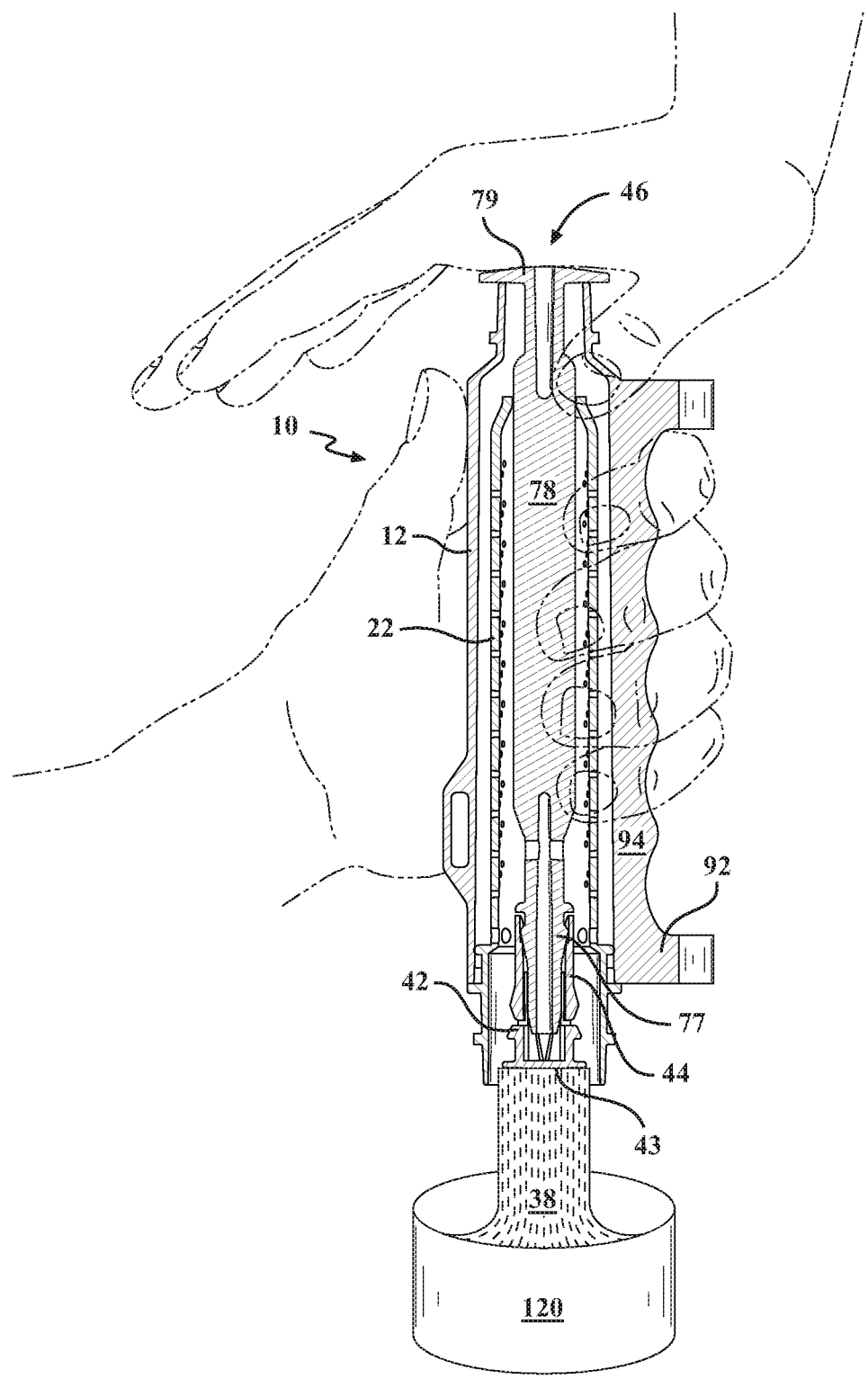
FIG. 7G is a cross-sectional view of the device of FIG. 7F with the plunger coupled to the piston in the first position.

Of course in many examples, as is illustrated in FIGS. 7E-7G, once the outlet cap 60 has been removed from the housing 12, the method further includes the step of coupling the plunger 78 to the piston 42 such that force can be applied to the piston 42 via the plunger 78 to move the piston 42 from the first position 45 to the second position 46 and discharge the composition 38 collected in the collection chamber 36 of the filter element 22 and into a container 120.

FIG. 7E is a cross-sectional view of the device of FIG. 7D with a decoupled inlet cap 48 to provide access so that the decoupled plunger 78 can be connected to the piston 42 and force can be applied to the plunger 78 to move the piston 42 from the first position 45 to the second position 46 to discharge the composition 38 from the device 10. In FIG. 7F the device 10 of FIG. 7E has the plunger coupled to the piston 42 in the first position. Then in FIG. 7G, force has been applied to the plunger 78 to move the piston from the first position 45 to the second position 46 to discharge the composition 38 from the device 10.

In many examples, the method further includes the step of decoupling the plunger 78 from the piston 42. In such examples, the method may also include the steps of coupling the inlet cap 48 to the housing 12 or the filter element 22 and coupling the outlet cap 60 to the housing 12. In turn, the steps of acquiring, collecting, decoupling the inlet cap 48, decoupling the outlet cap 60, and applying a force in a first direction to move the piston 42 from the first position 45 to the second position 46 to discharge the composition 38 from the filter element 22 are repeated at least once so that additional amounts of the composition 38 can be harvested with the device 10.

Of course, referring now to FIGS. 8A-9B, once removed, the method may further include the step of coupling the inlet cap 48 and the outlet cap 60 to one another to restore vacuum airflow to the surgical tool 54 subsequent to the steps of acquiring, collecting, decoupling the inlet cap 48, and decoupling the outlet cap 60.

Referring now to FIG. 1, an example of the device 10 is illustrated. Referring specifically to FIG. 1, the device 10 includes the housing 12 having: (1) a piston rack 92; (2) a grip 94; and (3) a clip mount 96 (e.g. for a drape clip).

The piston rack 92 is configured to hold the plunger 78 while not in use. In the example shown, the piston rack 92 includes a first and a second clamp 98, 100, which are configured to mechanically engage the plunger 78. The clamp(s) may be configured in a C-shape. FIG. 7C illustrates the plunger 78 engaged in the piston rack 92, while FIG. 7D illustrates the plunger 78 disengaged from the piston rack 92. The clamps may take the form of any suitable coupler configured to engage the plunger 78 while the piston 42 is not in use.

The plunger 78 of the exemplary device of FIG. 1 configured to releasably couple to the housing 12 of the device 10. In FIG. 1, is the plunger 78 is shown decoupled from the device 10. In FIG. 2A, the plunger 78 is shown mounted to the device 10 via the piston rack 92 located on the outer surface 19 of the outer wall 18 of the housing 12 which is shaped to cooperate with and releasably engage the plunger 78. In some such examples, the outer wall 18 of the housing 12 includes the plunger rack 92 comprising one or more features (in the example of FIG. 1, two features) which are shaped to releasably engage the plunger 78. As such, once the composition 38 is collected and the outlet cap 60 of the device 10 is removed, a user need not look for the plunger 78, the user can simply remove the plunger 78 from the piston rack 92 and couple the plunger 78 to the piston 42 so that the composition 38 can be discharged from the collection chamber 36 of the device 10 and ultimately harvested.

Referring now to FIGS. 7F and 7G, when the plunger 78 is disengaged, and for use and coupled to the piston 42 so that force can be applied to the piston 42 via the plunger 78 to move the piston 42 from a first position 45 to a second position 46 and discharge the composition 38 collected in the collection chamber 36, the grip is 94 is disposed on the outer wall 18 of the housing 12, the grip 94 can be used. That is, when the force is being applied to plunger 78 to move the piston 42 from a first position 45 to a second position 46 and discharge the composition 38, a user can robustly secure the housing 12 with one hand on the grip 94, and actuate or apply force to the plunger 78 with their other hand to move the piston 42 and harvest the composition 38. Various examples of the grip 94, e.g. with and without finger indents, comprising various "grip friendly" materials such as elastomers and foams are contemplated herein. The grip 94 facilitates user-friendly two-handed operation of the device 10, where a first hand is placed around the grip 94 and the other hand engages the plunger 78.

The device can also include a grip 94. The grip may be part of the piston rack 92 or may be stand alone and located on the outer wall 18 of the housing 12. The grip 94 provides the user with improved control of the device 10 during the harvesting of the composition 38. In the example of FIG. 1, as an additional benefit, once the plunger 78 is removed from the piston rack 92, the grip 94, which is part of the piston rack 92 in this example, is exposed so that when the piston 42 is coupled to the plunger 78 and force is applied to the plunger 78, the user can utilize the grip 94 to better hold the device 10 during the application of force to the plunger 78 and the ensuing discharge of the composition 38 from the collection chamber 36 of the device 10.

Referring again to FIGS. 1 and 2, the device may include a clip mount 96. A drape clip includes a clip which is configured to be releasably coupled to various surfaces, and fabrics in the operating room can be used with the clip mount 96. In the example shown, a spring-loaded V-drape clip is utilized; however, various other clip configurations known in the art can be used in lieu of the spring-loaded V-clip illustrated. As such, the device 10 can be conveniently stored (mounted) and easily located and accessed.

FIG. 4 is an isolated perspective view of the filter element 22 of the device 10 of FIG. 1. In this example, the plurality of apertures 34 are patterned in diagonal lines in the sidewall 28 of the filter element 22 to optimize the hydration of the composition 38 collected in the collection chamber 36. The plurality of apertures 34 (e.g. lines) are dispersed relatively evenly across, e.g. spread out on the filter element 22. In this example, the outer peripheral surface 32 of the sidewall 28 includes two tri-tipped ribs 88 extending longitudinally from the first end 24 toward the second end 26 of the filter element 22.

The device 10 of FIG. 1 includes the inlet cap 48 with the J-notch 102 (a first rotational coupler) therein, and the outer peripheral surface 32 of sidewall 28 of the first end 24 of the filter element 22 has the J-notch post 104 (second rotational coupler) thereon. Thus, the inlet cap 48 has a female configuration, and the first end 24 of the filter element 22 has a male configuration. The J-notch post 104 (second rotational coupler) of the first end 24 of the filter element 22 is inserted and rotated into the J-notch 102 (first rotational coupler) of the inlet cap 48 to releasably couple the filter element 22 to the inlet cap 48, the indicium 106 on the inlet cap 48 and the indicium 108 on the housing 12 line-up to indicate that the inlet cap 48 and the housing 12 are fully engaged (i.e., are sufficiently rotated relative to one another such that the two are fully engaged). Notably, the inlet cap 48 of this example cooperates with the vacuum spacer 66, which also has the J-notch post 110 thereon.

Referring FIG. 1 as well as FIGS. 5A and 5B, the device 10 includes the outlet cap 60 with the J-notch 112 therein, and the proximal end of the outer wall 18 of the housing 12 has the J-notch post 114 thereon. The outlet cap 60 has a female configuration, and the proximal end 16 of the housing 12 has a male configuration. When the J-notch post 114 of the proximal end of the outer wall 18 of the housing 12 is inserted and rotated into the J-notch 112 of the outlet cap 60 to releasably couple the housing 12 to the outlet cap 60, the indicium 116 on the outlet cap 60 and the indicium 118 on the housing 12 line-up to indicate that the outlet cap 60 and the housing 12 are fully engaged.

The J-notch and j-notch posts shown throughout this disclosure may have other suitable geometries that are coupled of facilitating rotational coupling between the caps 48, 60 and the housing 12, and between the caps 48, 60 themselves. In other words, any form of rotational coupler may be used interchangeably with the various j-notch and post configurations described above, so long as one of the components has a male rotational coupler configuration and the other component has a female rotational coupler configuration. Frictional engagement between the inlet and outlet caps 48, 60 and the housing 12, and between the inlet and outlet caps 48, 60 themselves is also contemplated.

The rotational engagement of the caps 48, 60 with the housing 12, particularly between the inlet cap 48 and the housing 12 facilitates intuitive decoupling, particularly when the assembly is under vacuum.

Referring now to FIGS. 14-20, a device 510 for collecting and processing bone fragments is disclosed. The device 510 includes a housing 512, a filter element 522, an inlet cap 548, and an outlet cap 560. The device 510 includes the housing 512, which includes a distal end 514, a proximal end 516, and an outer wall 518 extending between the distal and proximal ends 514, 516. The outer wall 518 has an outer surface 519 and an inner surface 520.

Figure 14:
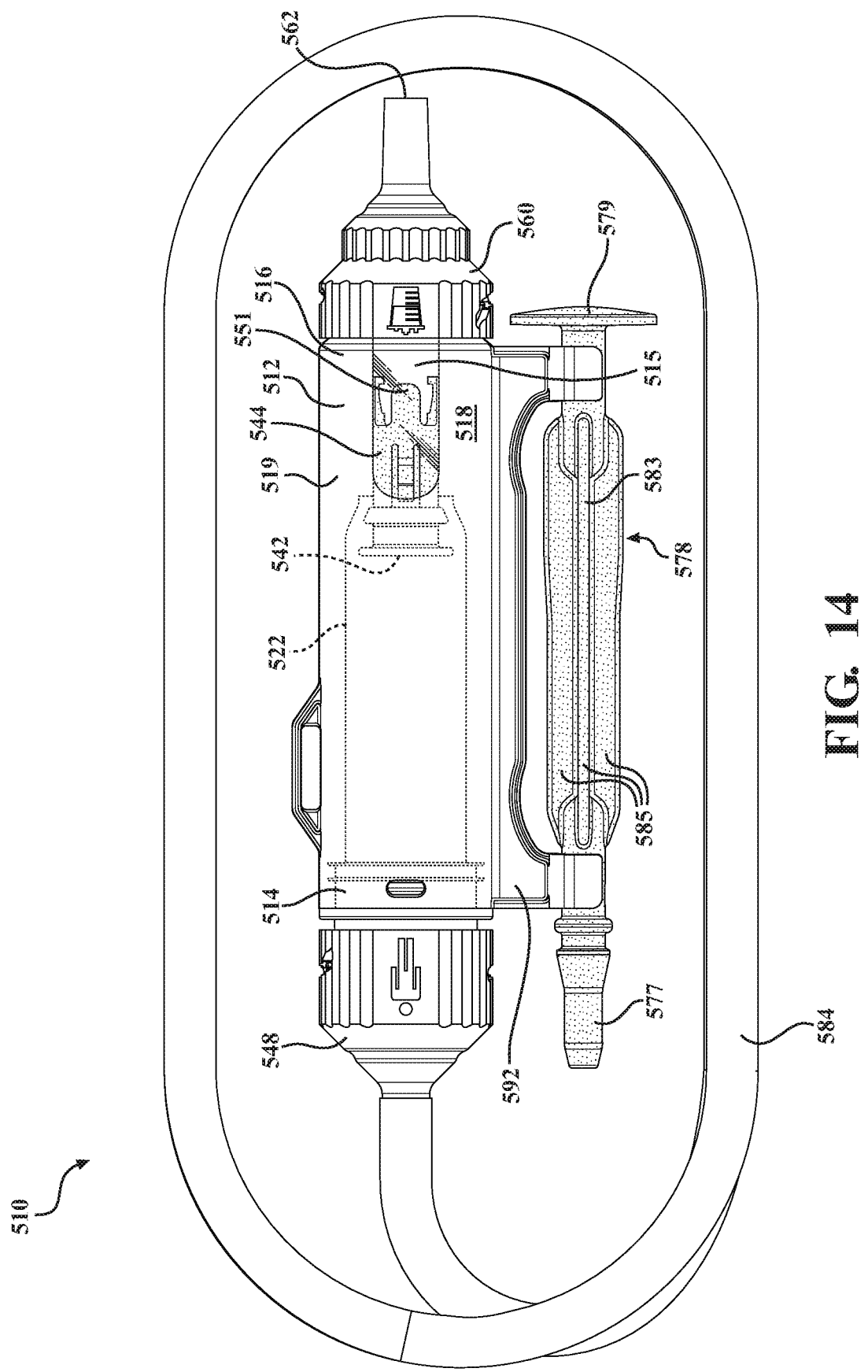
FIG. 14 is a perspective view of a device for collecting a composition comprising bone fragments.
Figure 15:
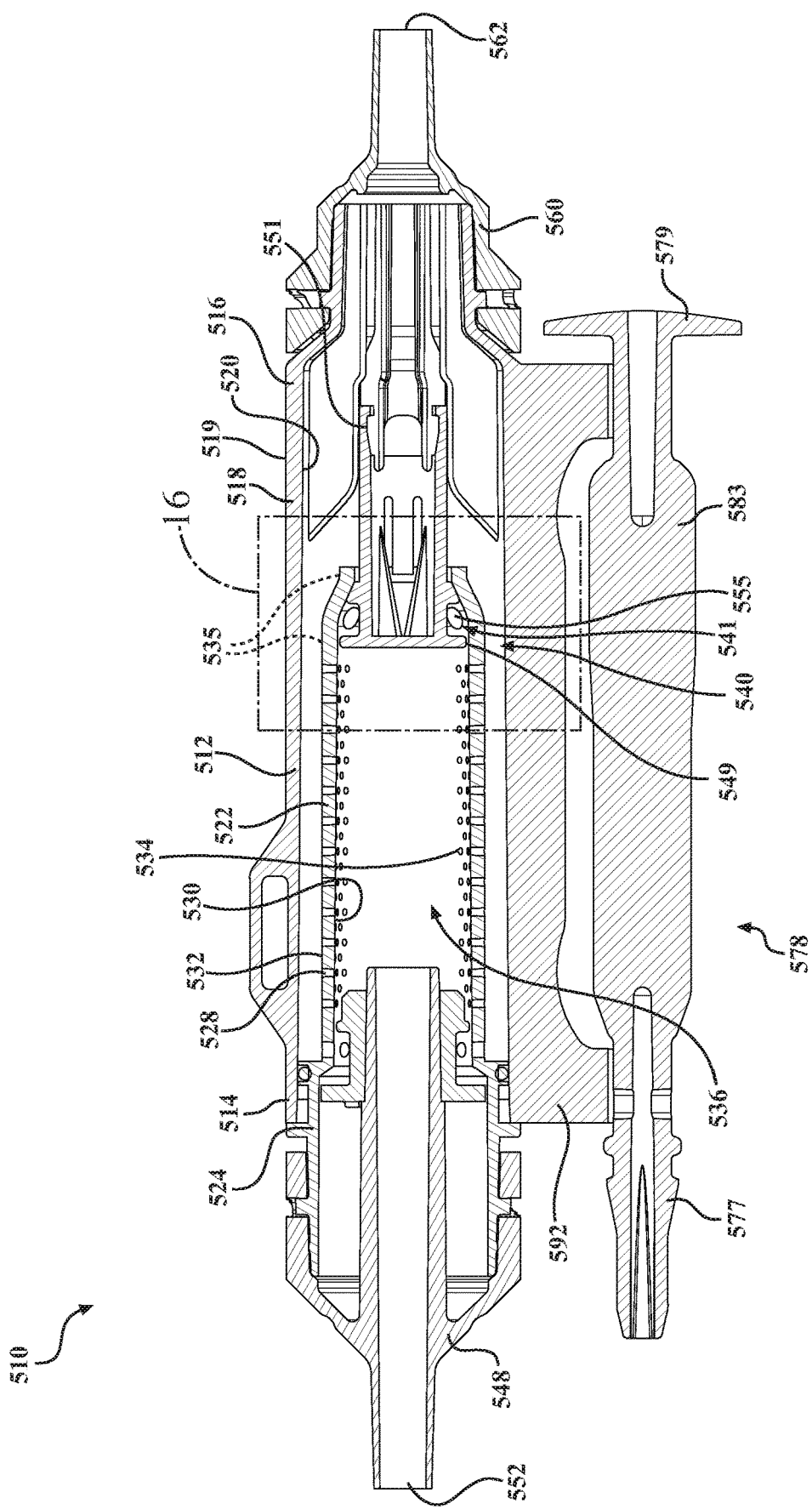
FIG. 15 is a cross-sectional view of the device of FIG. 14.

Referring now to FIGS. 14 and 15, the inlet cap 548 is shown releasably coupled to the distal end 514 of the housing 512 and/or a first end 524 of the filter element 522. The inlet cap 548 includes an intake port 552 configured to be coupled to a surgical tool and receive the composition comprising bone fragments, the filter element 522 collects the composition comprising bone fragments, and the outlet cap 560 is releasably coupled to the proximal end 516 of the housing 512 and includes a vacuum port 562 configured to be coupled to a vacuum source. In the exploded view of FIG. 17, a vacuum spacer 566 is shown separate from the inlet cap 548. The vacuum spacer 566 facilitates airtight connection of the inlet cap 548 to the device 510 and its separate fabrication simplifies molding and assembly of the inlet cap 548.

The filter element 522 is at least partially disposed within the housing 512. In FIG. 14, the filter element 522 within the housing 512 of the device 510 is illustrated in phantom. In the cross-sectional view of FIG. 15, the filter element 522 is shown partially disposed within the housing 512.

As is illustrated in the exploded view of the device 510 shown in FIG. 17, the filter element 522 has the first end 524 and the second end 526, which are joined by a sidewall 528. The first end 524 is positioned closer to the distal end 514 of the housing 512 than the second end 526. The sidewall 528 has a plurality of filter apertures 534 and defines an inner peripheral surface 530 and an outer peripheral surface 532. The inner peripheral surface 530 of the sidewall 528 at least partially defines a collection chamber 536 for collection of a composition comprising bone fragments.

As is shown in the cross-sectional view of FIG. 15, the outer peripheral surface 532 of the sidewall 528 and the inner surface 520 of the outer wall 518 are spaced apart from one another to define an exterior radial volume 540. The composition typically follows a primary communication path through the inlet cap 548 and into the collection chamber 536, wherein excess fluid is drawn through the plurality of filter apertures 534, into the exterior radial volume 540, and out of the outlet cap 560. During use, the composition is drawn into the collection chamber 536 of the filter element 522 and filtrate is drawn through a primary fluid communication path and out of the outlet cap 560.

Referring generally to FIGS. 17-20, the sidewall 528 also has a proximal portion 535 adjacent the second end 526 which defines at least one drain aperture 555. In this example, the proximal portion 535 of the sidewall 528 of the filter element 522 is tapered radially inward.

The device 510 of this example also includes a piston 542, part of which can be seen through a window portion 515 in the sidewall 528 of the device 510 in FIG. 14. As is illustrated in the cross-sectional view of the device 510 in FIG. 15 and in the exploded view of the device 510 shown in FIG. 17, the piston 542 includes a piston element 543 having a front face 545 and a back surface 547, a radial protrusion 580, and a plunger mount 544 opposite the piston element 543.

Figure 20:
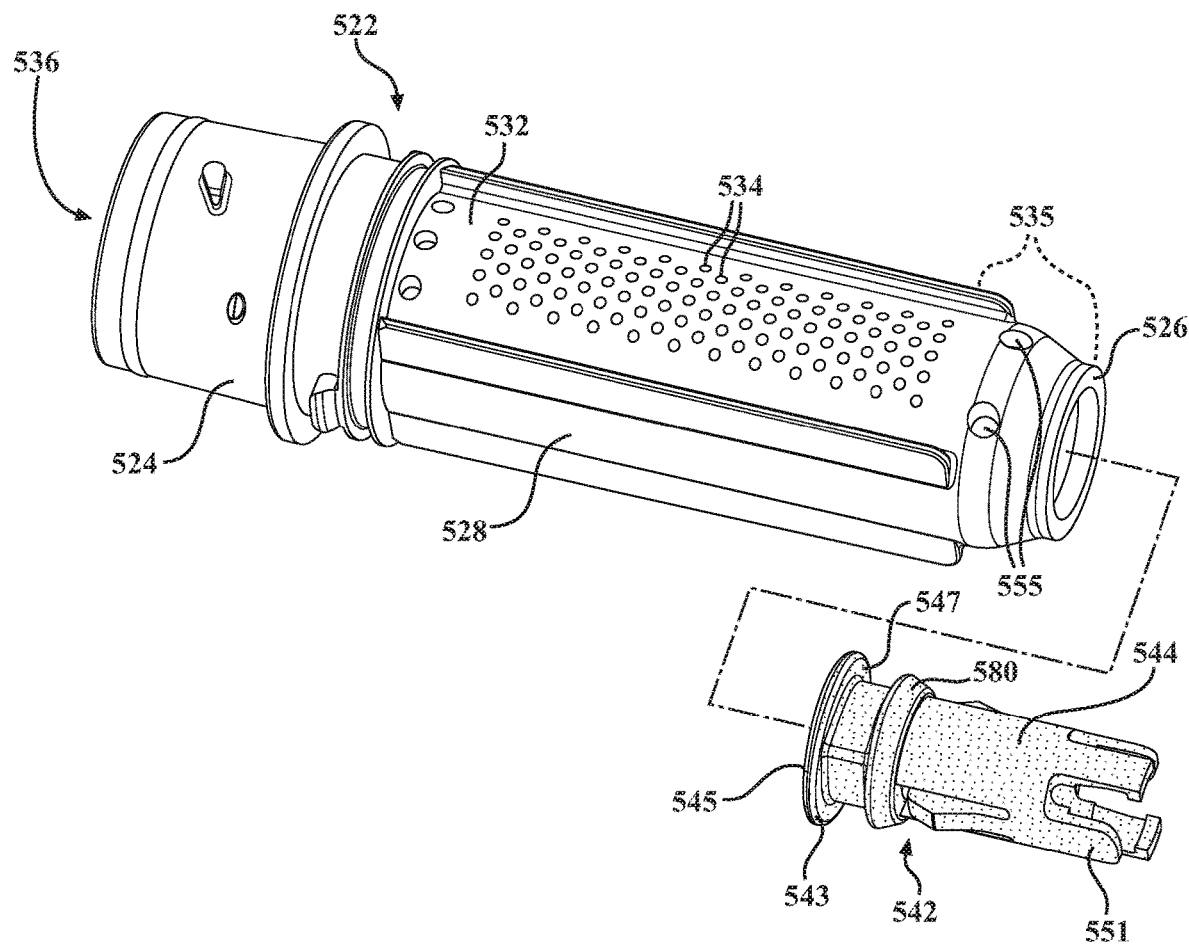
FIG. 20 is an exploded view of the filter element and the piston of FIG. 18.

The piston 542 is moveably disposed within the filter element 522. More specifically, the piston 542 is movable between a first and a second position. In the first position, the front face 545 of the piston element 543 at least partially defines the collection chamber 536 and the back surface 547, the plunger mount 544, and the inner peripheral surface 530 of the proximal portion 535 of the sidewall 528 define an interior radial volume 541. Further, in the first position, the front face 545 is within the filter element 522 and spaced distally relative to the second end 526 of the filter element 522 and the at least one drain aperture 555 places the exterior radial volume 540 and the interior radial volume 541 in fluid communication. FIG. 18 shows an isolated view of the piston 542 disposed in the filter element 522 in the first position, FIG. 19 shows a cross-sectional view of the piston 542 and the filter element 522 of claim 18, and FIG. 20 shows an exploded view of the piston 542 and the filter element 522 of claim 18.

During collection, the composition is acquired through the inlet cap 548 and collected in the collection chamber 536. As set forth above, the plurality of filter apertures 534 and exterior radial volume 540 provides the primary fluid communication path with the vacuum source. In this example, as is described in more detail below, a supplementary fluid communication path with the vacuum source runs around a perimeter of the piston element 543, through the interior radial volume 541, out the at least one drain aperture 555, and into the exterior radial volume.

Figure 16:
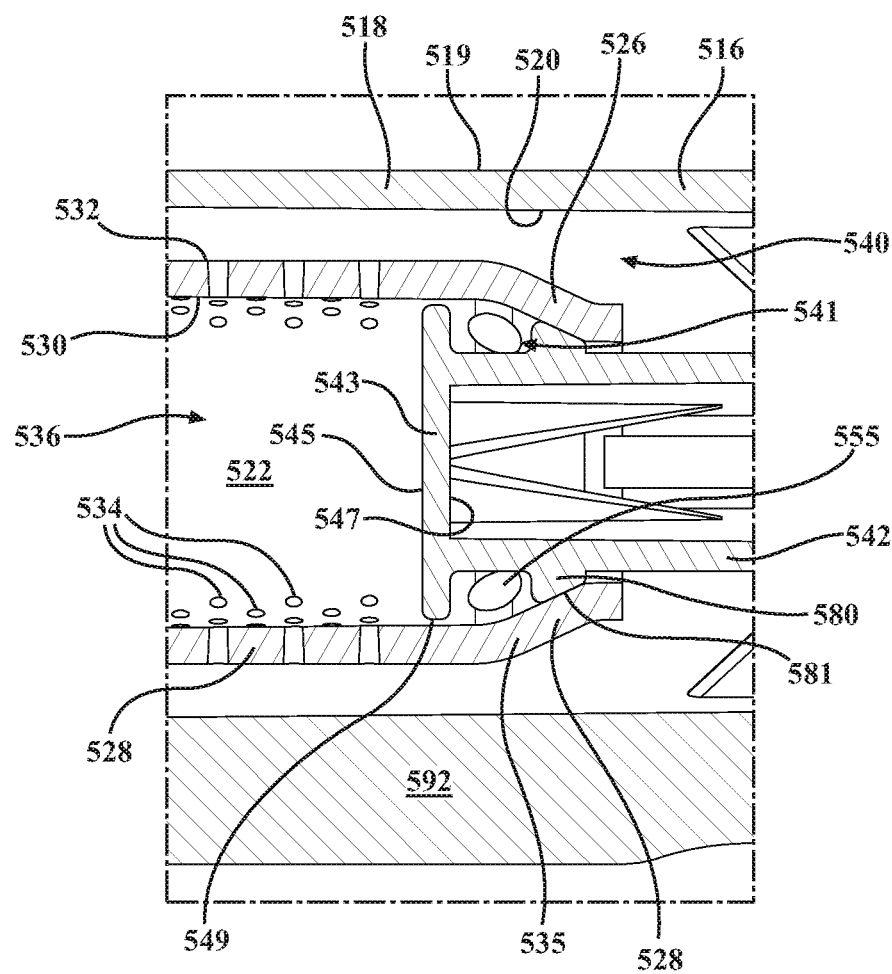
FIG. 16 is a close-up view of the distal end of the cross-sectional view of the device of FIG. 15 which illustrates a supplementary fluid communication path through a radial drain gap, an interior radial volume, and at least one drain aperture.

As is shown in the enlarged cross-sectional view of FIG. 16, in some examples where the proximal portion 535 of the filter element 522 is tapered radially inward, the radial protrusion 580 of the filter element 522 has a top surface 581 that is tapered radially inward. In such examples, the top surface 581 of the radial protrusion 580 abuts the inner peripheral surface 530 of the proximal portion 535 of the filter element 522, which is also tapered radially inward. As such, the radial protrusion 580 abuts the inner peripheral surface 530 of the proximal portion 535 of the filter element 522 when the piston 542 is in the first position.

As is shown in the enlarged cross-sectional view of FIG. 16, the piston element 543 of the piston 542 is spaced radially inwardly from the inner peripheral surface 530 of the sidewall 528 of the filter element 522 to define a radial drain gap 549. In other words, the radial drain gap 549 is a distance from the inner diameter of the filter element 522 to an outer diameter of the front face 545 of the piston element

543. The radial drain gap 549 is from 0.5 to 1, from 0.1 to 0.85, from 0.1 to 0.6, or from 0.14 to 0.54, mm when the piston 542 is in the first position. In various non-limiting examples, all gap width values and ranges of values including and between those described in the paragraph above are hereby expressly contemplated for use herein.

In some embodiments, the at least one drain aperture 555 on the proximal portion 535 of the sidewall 528 of the filter element 522 opens from 5 to 55 or from 5 to 25, % of a total surface area of an exterior peripheral surface of the proximal portion 535 of the sidewall 528. In various non-limiting examples, all surface area values and ranges of values including and between those described in the paragraph above are hereby expressly contemplated for use herein.

In some examples, the proximal portion 535 of the sidewall 528 of the filter element 522 has from 2 to 10, from 2 to 8, or from 2 to 6 drain apertures 555. The filter element 522 shown in FIGS. 17-20 has 4 drain apertures 555. Regarding the shape of the at least one drain aperture 555, the drain apertures 555 can have various shapes, e.g. ovular, elliptical, or polygonal shape. In a typical example the at least one drain aperture 555 is elliptical in shape, e.g. round. When more than one drain aperture 555 is included on the sidewall 528, the drain apertures 555 can have different shapes.

Regarding size of the at least one drain aperture 555, each of the at least one drain apertures 555 can have a diameter of from 0.1 to 4.5, or from 1.5 to 3.5, or from 2.8 to 3.2, mm. In many such examples, a diameter of each of the plurality of filter apertures 534 is from 0.1 to 2.5, from 0.75 to 1.25, or from 0.84 to 1.14, mm. In various non-limiting examples, all diameter values and ranges of values including and between those described in the paragraph above are hereby expressly contemplated for use herein.

Each of the at least one drain apertures 555 typically has a larger size than each of the plurality of filter apertures 534. In some examples, each of the at least one drain aperture 555 has a drain aperture 555 diameter at least two times larger than a filter aperture diameter of each of the filter apertures 534 in the sidewall 528 of the filter element 522.

From a practical perspective, the at least one drain aperture 555 (1) prevents collection of filtrate in the interior radial volume 541 and (2) provides improved filtration and drainage. Referring now to the enlarged, cross sectional view shown in FIG. 16, the supplementary fluid communication path runs through the radial drain gap 549, into the interior radial volume 541, out of the at least one drain apertures 555, into the exterior radial volume 540, and out of the outlet cap 560. That is, during use, the composition is drawn into the collection chamber 536 of the filter element 522 and filtrate is drawn through a supplementary fluid communication path and out of the outlet cap 560. As such, it provides an alternative fluid passage to the primary fluid communication path. It should be appreciated that the radial drain gap 549 is particularly effective because it provides drainage continuously along the inner peripheral surface 530 of the sidewall 528 of the filter element 522. The continuous profile of the radial drain gap 549 and the larger size of the at least one drain aperture 555 make the supplementary fluid communication path surprisingly effective.

Referring back to FIG. 14, the device 510 includes a plunger 578 configured to be releasably coupled to the piston 542 to move the piston 542 between the first and second positions. That is, upon removal of the inlet cap 548 and the outlet cap 560, the plunger 578 can be coupled to the piston 542, and force can be applied to the piston 542 to move the piston 542 from the first position to the second position to discharge composition from the filter element 522.

Figure 21:
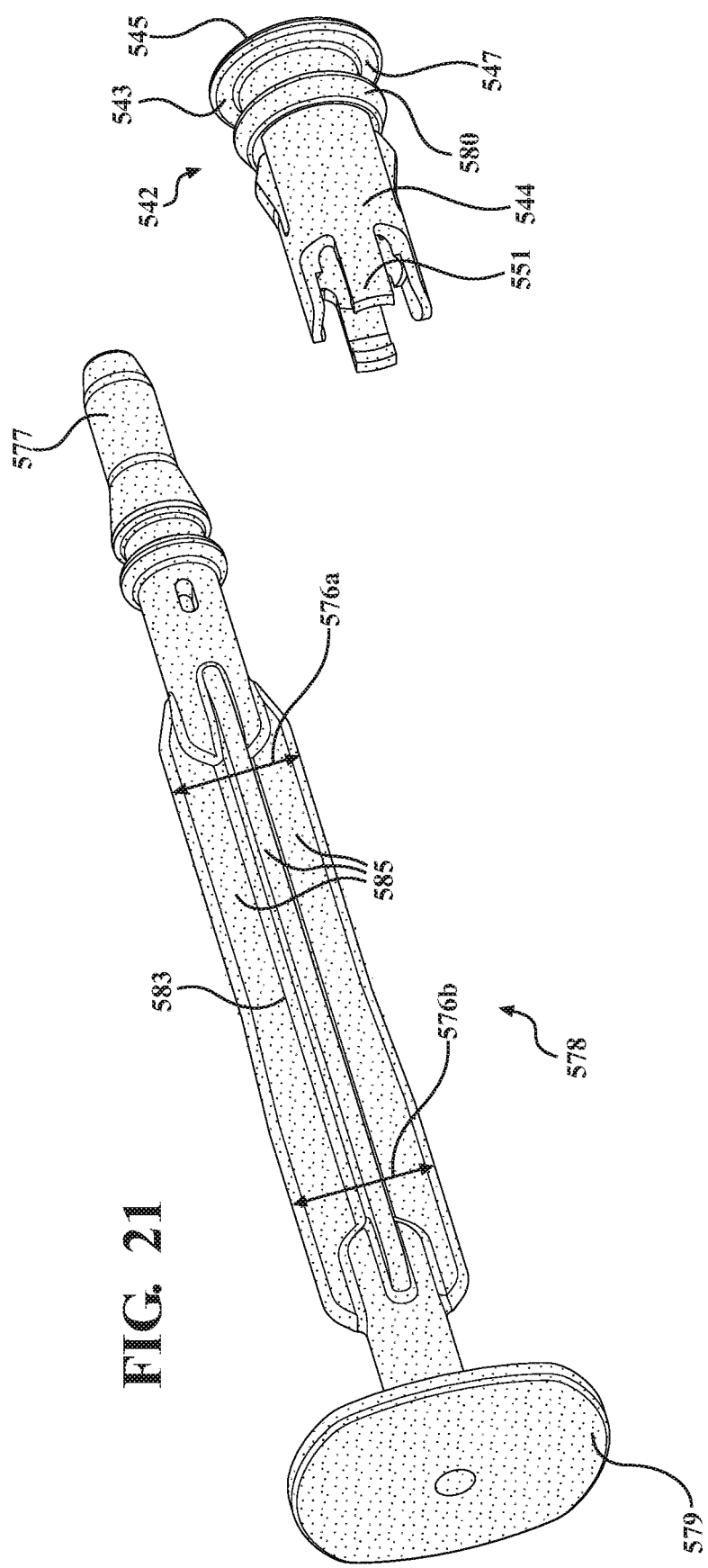
FIG. 21 is a perspective view of a piston and a plunger, which are configured to be releasably coupled to one another.
Figure 22:
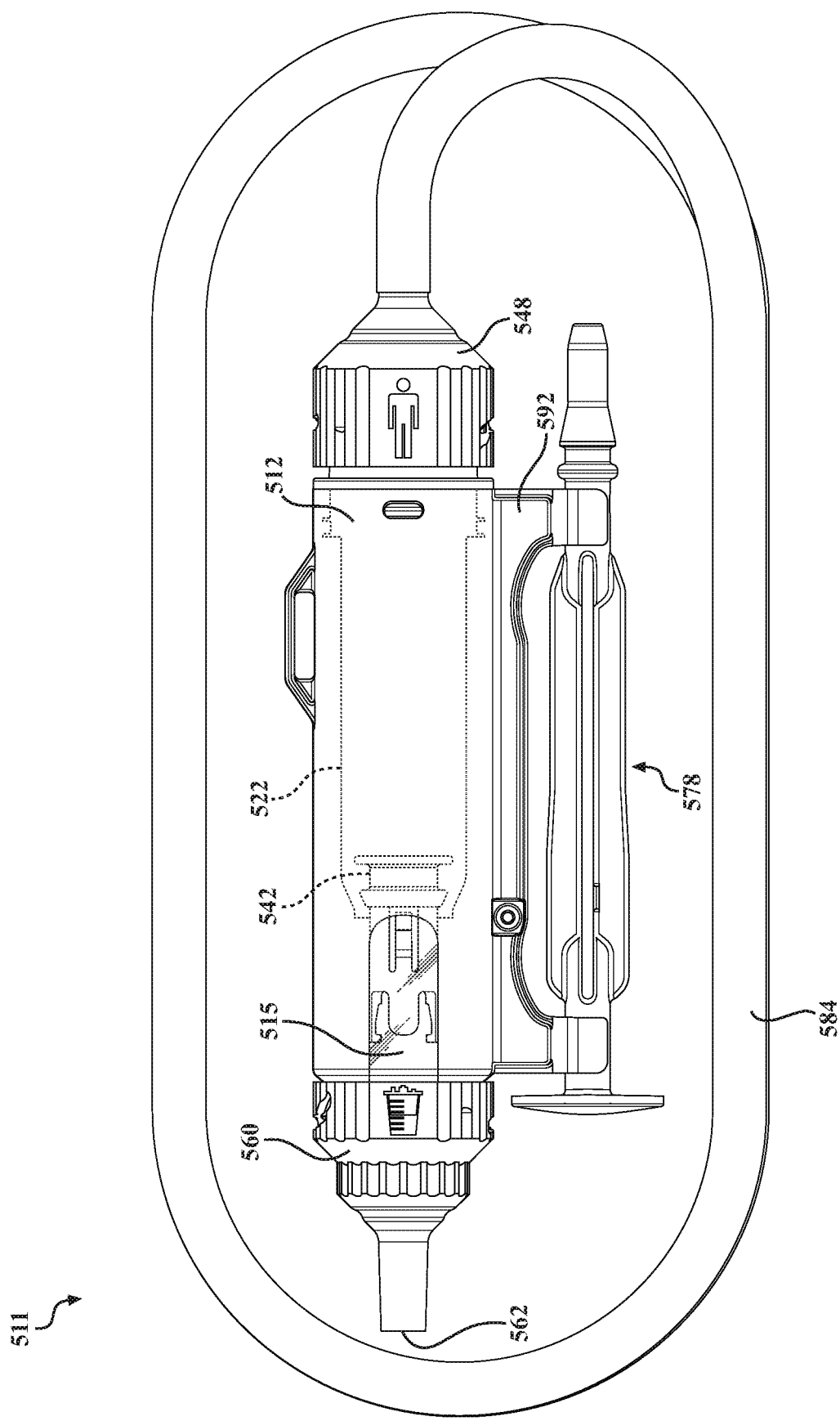
FIG. 22 is a perspective view of a device for collecting a composition comprising bone fragments which is sterilized.

Referring now to FIG. 21, the plunger 578 includes a corresponding attachment element 577, a press pad 579, and a body 583 extending therebetween. It should be appreciated that the press pad 579 of this disclosure could also be described as a handle and can be broadly interpreted as a surface to which force can be applied to the plunger 578 to move the piston 542 from the first position to the second position. The plunger mount 544 of the piston 542 includes an attachment element 551 that is shaped to releasably couple to the corresponding attachment element 577 of the plunger 578 to couple the plunger 578 to the piston 542. In some examples, the body 583 of the plunger 578 is tapered such that a diameter of the body 583 increases as the body 583 extends from the corresponding attachment element 577 towards the press pad 579. Still referring to FIG. 21, in some examples, the body 583 is tapered such that a diameter of the body 583 increases as the body 583 extends from the corresponding attachment element 577 towards the press pad 579. Further, the body 583 of the plunger 578 includes a plurality of ribs 585. The ribs 585 reduce the plastic content and the cost while having an I-beam like strengthening effect on the plunger 578. In the example of FIG. 14, the body 583 includes 4 tapered ribs 585. This tapering provides an interference fit which slows down the plunger 578 as it progresses through an opening at the second end 526 of the filter element 522 as the piston 542 is driven from the first position to the second position to eject composition/bone fragments collected in a controlled manner. In other words, the body 583 having a tapered profile prevents the plunger 578 and the piston 542 from violently shooting through the collection chamber 536 of the filter element 522 and out of the housing 512 of the device 510, which minimizes potential for the disconnection of the piston 542 and plunger 578 and/or an uncontrolled ejection of the composition collected out of the device 510. It should be appreciated that this plunger 578, with its tapered body 583, can be employed with any of the example devices described herein.

In FIG. 21, the increase of diameter of the body 583 of the plunger 578 as the body 583 extends from the corresponding attachment element 577 towards the press pad 579 is illustrated. For example, the diameter 576*a* of the body 583 proximal the press pad 579 is larger than the diameter 576*b* of the body 583 proximal the corresponding attachment element 577. In the example of FIG. 4, the tapering is accomplished via decreasing a width of the ribs 524 as they extend from the press pad 579 to the corresponding attachment element 577. It should be appreciated that the tapering can be consistent or inconsistent, e.g. with steps. In such examples, force that is required to be applied to the plunger 578 to move the piston 542 progressively increases as a plunger 578 is used to move the piston 542 between the first and second positions.

The outer wall 518 of the housing 512 of the device 510 has the window portion 515 which allows light to pass therethrough. The window portion 515 is typically located closer to the proximal end 516 of the housing 512 than to the distal end 514 of the housing 512. Typically, the window portion 515 is transparent. However, various examples of the device 510 may utilize the window portion 515 which is translucent, e.g. offers limited visibility.

Referring back again to FIG. 14, the window portion 515 is transparent. As such, the internal components of the device 510 are visible through the window portion 515. In many examples, the outer wall 518 includes a remaining portion in addition to and different than the window portion 515. In such examples, the remaining portion is translucent or opaque.

The piston 542 is at least partially visible through the window portion 515 in the outer wall 518 of the housing 512. In FIG. 14, the attachment element 551 of the plunger mount 544 of the piston 542 is visible through the window portion 515. Upon removal of the inlet cap 548 and the outlet cap 560, the plunger 578 can be coupled to the piston 542 while being viewed through the window portion 515. The visible engagement is user friendly and facilitates the proper and efficient use of the device 510. Once attached to the piston 542, force can be applied to the plunger 578 to move the piston 542 from the first position to the second position to discharge composition from the filter element 522.

In the example of FIG. 14, the attachment element 551 of the piston 542 is shaped to snap fit couple to the corresponding attachment element 577 of the plunger 578 to couple the plunger 578 to the piston 542. In other examples, the attachment element 551 of the piston 542 is shaped to threadedly couple to the corresponding attachment element 577 of the plunger 578 to couple the plunger 578 to the piston 542.

In some examples, the attachment element 551 of the piston 542 has a visual identifier and at least a portion of the corresponding attachment element 577 of the plunger 578 has a corresponding visual identifier that produce a visual association between the attachment element 551 of the piston 542, which is visible through the window portion 515 in the first position and the corresponding attachment element 577 of the plunger 578. The visual identifier can be corresponding indicia or even a matching color. The visual identifier and the corresponding visual identifier promote the insertion of the plunger 578 into the proximal end 516 of the housing 512, to further facilitate the proper and efficient use of the device 510.

In some specific examples, the visual identifier of the attachment element 551 of the piston 542 is a color, the corresponding visual identifier of the corresponding attachment element 577 of the plunger 578 is the color, and remaining components of the bone dust collector are collectively colored to maintain the visual association between the attachment element 551 of the piston 542 and the corresponding attachment element 577 of the plunger 578. In FIGS. 14 and 21, the visual identifier is a color represented by the stippling (dotted fill) of the plunger 578 and the piston 542. That is, in the example shown, the plunger 578 and the piston 542 are the same color as represented by the stippling, e.g. orange.

It should be appreciated that the visual identifiers on the piston 542 and the plunger 578 as well as the window portion 515 can be employed with any of the example devices described herein.

Referring now to FIGS. 22-26, a sterile bone collection device 511 and packaging system 700 is also disclosed. The sterile device 511 is just as described in the examples above but is sterilized. When packaged, the sterile device 511 includes a housing 512 including the distal end 514, the proximal end 516, and the outer wall 518 having a plunger rack 592 thereon. The plunger 578 is engaged in the plunger rack 592, the inlet cap 548 comprising the intake port 552 is releasably coupled to the distal end 514 of the housing 512, the intake tube 584 is connected to the intake port 552, and the outlet cap 560 is releasably coupled to the proximal end 516 of the housing 512. This assembled configuration is user friendly and allows a user to quickly understand the sterile device 511 and its assembly and dis-assembly, which is required to use the plunger 578.

Further, the sterile device 511 is removed from the packaging system 700 with the intake tube 584 attached to the proper end (i.e. the inlet cap 548) of the sterile device 511. In view of the pre-assembly and the sterilized state of the sterile device 511, the sterile device 511 can be removed from the packaging system 700 and used immediately. That is, the sterile device 511 can be removed from the packaging system 700 and a surgical tool can be immediately attached and used. Handling of the sterile device 511 prior to surgery is minimized and efficient use during surgery is facilitated.

Figure 23:
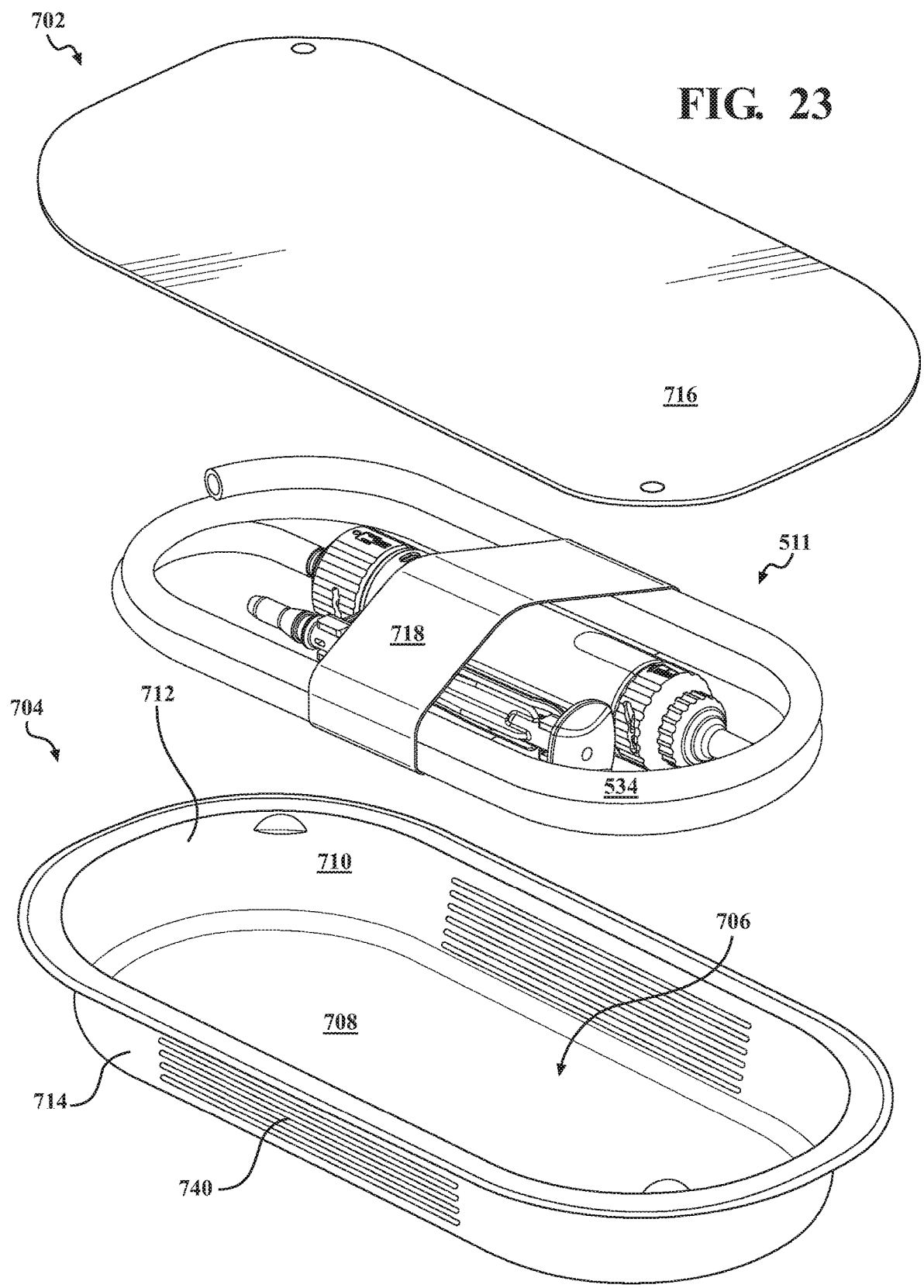
FIG. 23 is a perspective view of an inner blister pack of a packaging system for the sterilized device of FIG. 22.

Referring now to FIG. 23, the packaging system 700 includes an inner blister pack 702. The inner blister pack 702 includes an inner shell 704 that defines a sterile interior space 706 and that is configured to house the sterile device 511. Typically, the inner shell 704 includes a shell floor 708 and a shell sidewall 710 having the inner surface 712, an outer surface 714, and an ovular profile. The inner surface 712 of the shell sidewall 710 defines the sterile interior space 706 and houses the sterile device 511. The sterile device 511 is housed in the sterile interior space 706 with the intake tube 584 wrapped radially thereabout having an ovular circumferential profile that corresponds with the ovular profile of the shell sidewall 710. In some examples, a holding band 718 configured to hold the sterile device 511 with the intake tube 584 wrapped radially thereabout together is included in the packaging system 700. Finally, an inner sealing film 716 cooperates with the inner shell 704 to seal the sterile device 511 within the inner blister pack 702.

Figure 24:
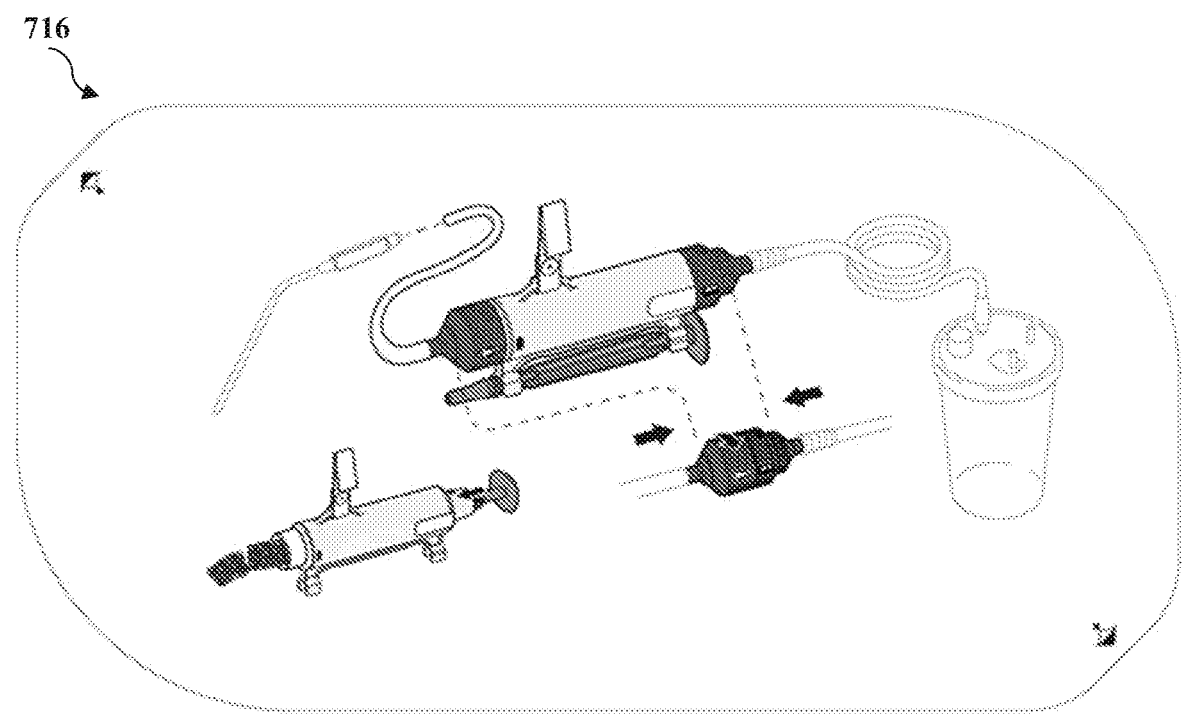
FIG. 24 is an inner sealing film for use with the inner blister pack having instruction graphics displayed thereon.

Referring now to FIG. 24, the inner sealing film 716 can have instruction graphics displayed thereon so that when a user opens the inner blister pack, presumably in a sterile zone, a user can refer to a sterile set of instructions for use. An inner sealing film 716 with instruction graphics displayed thereon is included in the appendix filed herewith. The sterile zone is a specific area in an operating room that is considered sterile and free of microorganisms. Maintaining the sterile zone is not an easy task because there are many chances for a breach in sterility during set-up, operation, and post-operation. With this packaging system 700, the sterile device 511, including directions for use, can be utilized in a sterile and efficient manner right in the sterile zone of the operating room. In fact, the inner blister pack 702 with the directions thereon and the sterile device 511 therein can be conveniently positioned in the sterile zone on patient support apparatus or elsewhere before surgery.

Figure 25:
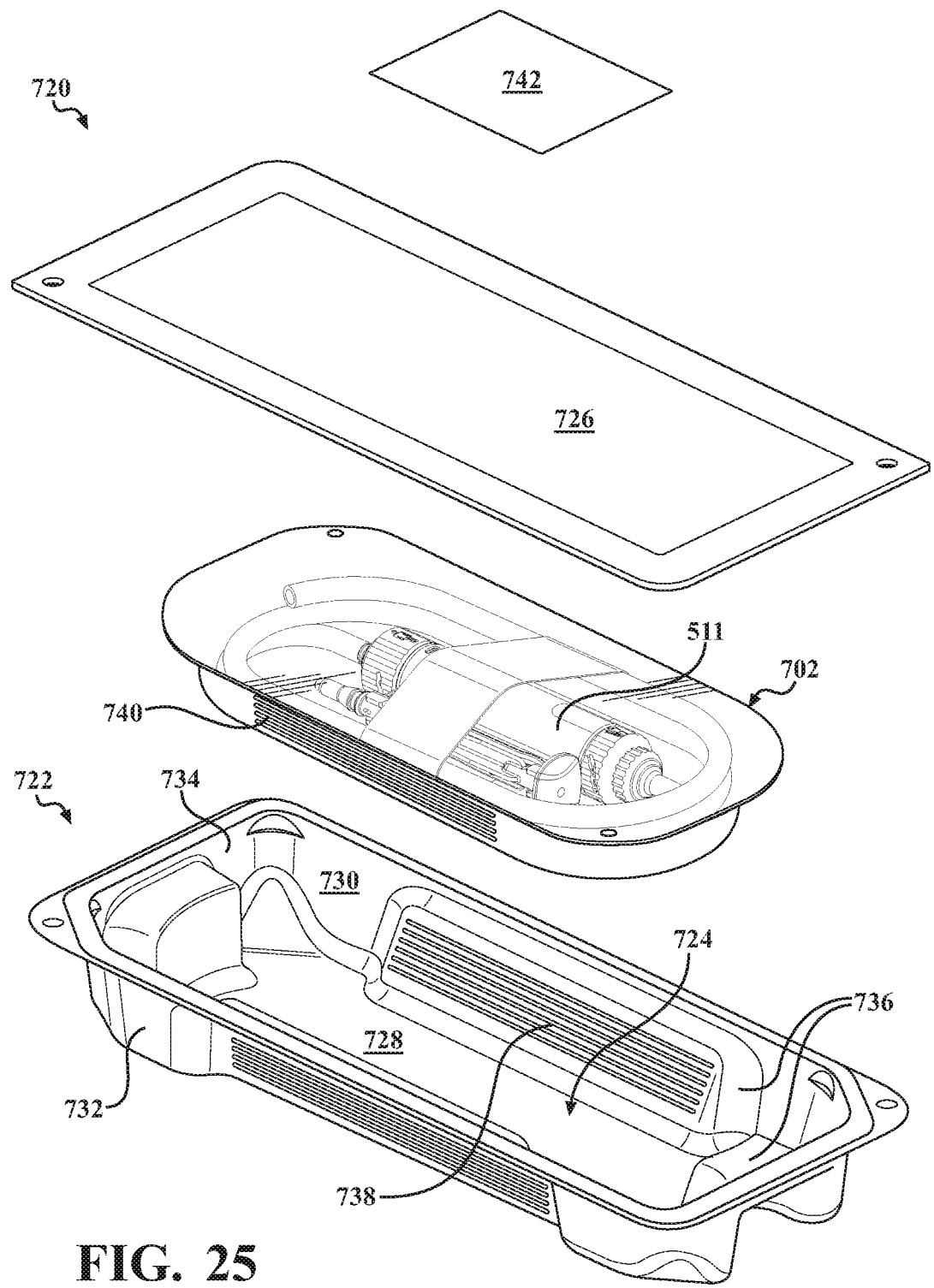
FIG. 25 is an outer blister pack of the packaging system for optional use with the inner blister pack of FIG. 23.

Referring now to FIG. 25, the packaging system 700 may also include an outer blister pack 720. If included in the packaging system 700, the outer blister pack 720 includes a barrier shell 722 that defines a sterile chamber 724 and that is configured to house the inner blister pack 702. A barrier sealing film 726 cooperates with the barrier shell 722 to seal the inner blister pack 702 within the outer blister pack 720. The barrier shell 722 includes a barrier floor 728 and a barrier sidewall 730 having an exterior surface 732 and an interior surface 734. The packaging system 700 may also include a packaging label 742.

In some examples where the packaging system 700 includes the inner and the outer blister packs 702, 720, the barrier sidewall 730 includes one or more tabs 736 projecting radially inwardly from the barrier sidewall 730 into the sterile chamber 724 which cooperate with the outer surface 714 of the shell sidewall 710 of the inner shell 704 to secure the inner blister pack 702 in the sterile chamber 724 of the outer blister pack 720. Further, the one or more tabs 736 can have a contact surface 738 which is shaped to releasably couple with a corresponding contact surface 740 on the outer surface of the shell sidewall 710. For example, still referring to FIG. 25, two of the tabs 736 have a ridged contact surface 738 which cooperates with a corresponding ridged contact surface 740 on the outer surface 714 of the shell sidewall 710 to secure the inner blister pack 702 within the sterile chamber 724 of the outer blister pack 720.

Figure 26:
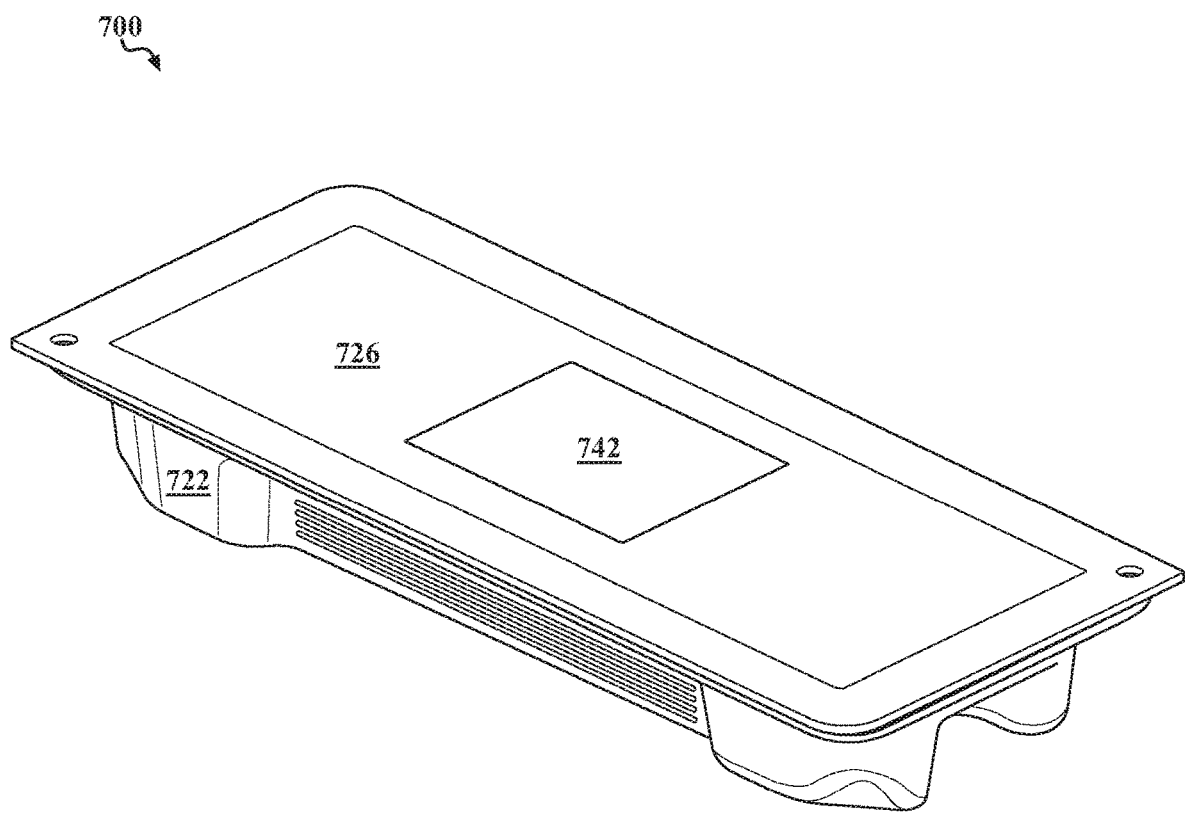
FIG. 26 is a perspective view of an assembled packaging system with the sterile bone collection device of FIG. 22.

FIG. 26 is a perspective view of the packaging system 700 with the sterile bone collection device 511 therein.

It will be appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several examples have been discussed in the foregoing description. However, the examples discussed herein are not intended to be exhaustive or limit the device to any particular form. The terminology which has been used is intended to be in the nature of words of description rather than of limitation. Many modifications and variations are possible in light of the above teachings and the device may be practiced otherwise than as specifically described.

What is claimed is:

1. A device for collecting and processing bone fragments, said device comprising:
   a housing including a distal end, a proximal end, and an outer wall having an inner surface extending between said distal and proximal ends;
   a filter element at least partially disposed within said housing, said filter element having:
      a first end;
      a second end, said first end positioned closer to said distal end of said housing than said second end;
      a sidewall joining said first end and said second end, said sidewall defining an inner peripheral surface and an outer peripheral surface, said sidewall having a plurality of filter apertures therein, wherein said inner peripheral surface of said sidewall at least partially defines a collection chamber for collection of a composition comprising bone fragments, and said outer peripheral surface of said sidewall and said inner surface of said outer wall are spaced apart from one another to define an exterior radial volume; and
      a proximal portion adjacent said second end which defines at least one drain aperture;
   a piston including:
      a piston element having a front face and a back surface; and
      a plunger mount opposite said piston element and having a radial protrusion,
      said piston moveably disposed within said filter element and movable between a first and a second position, wherein in said first position:
         said front face of said piston element at least partially defines said collection chamber;
         said back surface, said plunger mount, and said inner peripheral surface of said proximal portion of said sidewall define an interior radial volume; and
         said front face is within said filter element and spaced distally relative to said second end of said filter element and said at least one drain aperture places said exterior radial volume and said interior radial volume in fluid communication;
   an intake port configured to be coupled to a surgical tool and receive said composition comprising bone fragments; and
   a vacuum port configured to be coupled to a vacuum source;
   wherein said interior radial volume provides a supplementary fluid communication path through said at least one drain aperture.

2. The device as set forth in claim 1 wherein said proximal portion of said filter element is tapered radially inward.

3. The device as set forth in claim 2 wherein said radial protrusion has a top surface that is tapered radially inward such that said top surface abuts said inner peripheral surface of said proximal portion of said filter element, which is also tapered radially inward, when said piston is in said first position.

4. The device as set forth in claim 1 wherein said piston element of said piston is spaced radially inwardly from said inner peripheral surface of said sidewall of said filter element to define a radial drain gap.

5. The device as set forth in claim 4 wherein said radial drain gap is from 0.05 to 1 mm when said piston is in said first position.

6. The device as set forth in claim 1 wherein said at least one drain aperture on said proximal portion of said sidewall of said filter element opens from 5 to 55% of a total surface area of an exterior peripheral surface of said proximal portion of said sidewall.

7. The device as set forth in claim 1 wherein said at least one drain aperture is further defined as from 2 to 10 drain apertures.

8. The device as set forth in claim 1 wherein said at least one drain aperture is elliptical and has a diameter of from 0.1 to 4.5 mm.

9. The device as set forth in claim 1 wherein said at least one drain aperture has a drain aperture diameter at least two times larger than a filter aperture diameter of at least one of said plurality of apertures in said sidewall of said filter element.

10. The device as set forth in claim 1 further comprising a plunger configured to be releasably coupled to said piston to move said piston between said first and second positions, said plunger comprising a corresponding attachment element, a press pad, and a tapered body extending therebetween, wherein said body is tapered such that a diameter of said body increases as said body extends from said corresponding attachment element towards said press pad.

11. A device for collecting and processing bone fragments, said device comprising:
   a housing having a distal end and a proximal end, said housing comprising an outer wall having an inner surface extending between said distal end and said proximal end and a window portion which allows light to pass therethrough;
   a filter element at least partially disposed within said housing, said filter element having:
      a first end;
      a second end, said first end positioned closer to said distal end of said housing than said second end;
      a sidewall joining said first end and said second end, said sidewall defining an inner peripheral surface and an outer peripheral surface, said sidewall having a plurality of apertures therein, wherein said inner peripheral surface of said sidewall at least partially defines a collection chamber for collection of a composition comprising bone fragments, said outer peripheral surface of said sidewall and said inner surface of said outer wall are spaced apart from one another to define an exterior radial volume; and a piston moveably disposed within said filter element and movable between a first and a second position, wherein said piston at least partially defines said collection chamber in said first position and is at least partially visible through said window portion in said outer wall;

an intake port configured to be coupled to a surgical tool and receive said composition comprising bone fragments;

a vacuum port configured to be coupled to a vacuum source; and a plunger configured to be releasably coupled to said piston to move said piston between said first and second positions, wherein said plunger can be coupled to said piston while being viewed through said window, and force can be applied to said piston to move said piston from said first position to said second position to discharge composition from said filter element.

12. The device as set forth in claim 11 wherein said window portion is transparent.

13. The device as set forth in claim 11 wherein said outer wall includes a remaining portion in addition to and different than said window portion and said remaining portion is translucent or opaque.

14. The device as set forth in claim 11 wherein said piston includes a piston element and a plunger mount opposite said piston element and said plunger mount is visible through said window portion in said first position.

15. The device as set forth in claim 14 wherein said plunger mount of said piston includes an attachment element and said plunger includes a corresponding attachment element, wherein said attachment element of said piston is shaped to releasably couple to said corresponding attachment element of said plunger to couple said plunger to said piston.

16. The device as set forth in claim 15 wherein said attachment element of said piston is shaped to snap fit couple to said corresponding attachment element of said plunger to couple said plunger to said piston.

17. The device as set forth in claim 15 wherein said attachment element of said piston is shaped to threadedly couple to said corresponding attachment element of said plunger to couple said plunger to said piston.

18. The device as set forth in claim 15 wherein said attachment element of said piston has a visual identifier, which is visible through said window portion in said first position, and at least a portion of said corresponding attachment element of said plunger has a corresponding visual identifier that produce a visual association between said attachment element of said piston and said corresponding attachment element of said plunger to promote the insertion of said plunger into said proximal end of said housing.

19. The device as set forth in claim 18 wherein said visual identifier of said attachment element of said piston is a color, said corresponding visual identifier of said corresponding attachment element of said plunger is said color, and remaining components of said device are collectively colored to maintain the visual association between said attachment element of said piston and said corresponding attachment element of said plunger.

20. A device for collecting and processing bone fragments, said device comprising:

a housing having a distal end and a proximal end, said housing comprising an outer wall having an inner surface extending between said distal end and said proximal end;

a filter element at least partially disposed within said housing, said filter element having:
a first end;
a second end, said first end positioned closer to said distal end of said housing than said second end;
a sidewall joining said first end and said second end, said sidewall defining an inner peripheral surface and an outer peripheral surface, said sidewall having a plurality of apertures therein, wherein said inner peripheral surface of said sidewall at least partially defines a collection chamber for collection of a composition comprising bone fragments, said outer peripheral surface of said sidewall and said inner surface of said outer wall are spaced apart from one another to define an exterior radial volume; and a piston comprising an attachment element and moveably disposed within said filter element and movable between a first and a second position, wherein said piston at least partially defines said collection chamber in said first position;

an inlet cap releasably coupled to said distal end of said housing and/or said first end of said filter element, said inlet cap including an intake port configured to be coupled to a surgical tool and receive said composition comprising bone fragments;

an outlet cap releasably coupled to said proximal end of said housing, said outlet cap including a vacuum port configured to be coupled to a vacuum source; and a plunger configured to be releasably coupled to said piston to move said piston between said first and second positions, said plunger comprising a corresponding attachment element, a press pad, and a tapered body extending therebetween, wherein said body is tapered such that a diameter of said body increases as said body extends from said corresponding attachment element towards said press pad, wherein upon removal of said inlet cap and said outlet cap, said plunger can be coupled to said piston, and force can be applied to said piston to move said piston from said first position to said second position to discharge composition from said filter element.

* * * * *